US008481535B2

(12) United States Patent
Gharbaoui et al.

(10) Patent No.: US 8,481,535 B2
(45) Date of Patent: Jul. 9, 2013

(54) CRYSTALLINE FORMS AND PROCESSES FOR THE PREPARATION OF PHENYL-PYRAZOLES USEFUL AS MODULATORS OF THE 5-HT$_{2A}$ SEROTONIN RECEPTOR

(75) Inventors: Tawfik Gharbaoui, Escondido, CA (US); Dipanjan Sengupta, San Diego, CA (US); Ashwin M. Krishnan, San Diego, CA (US); Nainesh Shah, Rensselner, NY (US); Ryan M. Hart, San Francisco, CA (US); Mark Macias, San Diego, CA (US); Edward A. Lally, La Jolla, CA (US); Jonathan Duffield, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 1007 days.

(21) Appl. No.: 12/301,212

(22) PCT Filed: May 17, 2007

(86) PCT No.: PCT/US2007/011810
§ 371 (c)(1),
(2), (4) Date: Jul. 1, 2009

(87) PCT Pub. No.: WO2007/136689
PCT Pub. Date: Nov. 29, 2007

(65) Prior Publication Data
US 2010/0234380 A1 Sep. 16, 2010

Related U.S. Application Data

(60) Provisional application No. 60/801,789, filed on May 18, 2006, provisional application No. 60/921,318, filed on Apr. 2, 2007.

(51) Int. Cl.
*A61K 31/5377* (2006.01)
*A61K 31/496* (2006.01)
*C07D 295/185* (2006.01)
*C07D 403/12* (2006.01)

(52) U.S. Cl.
USPC .......... 514/236.5; 514/254.05; 544/107; 544/371

(58) Field of Classification Search
None
See application file for complete search history.

(56) References Cited

U.S. PATENT DOCUMENTS

| | | |
|---|---|---|
| 4,099,012 A | 7/1978 | Gschwend |
| 4,405,644 A | 9/1983 | Kabbe et al. |
| 4,409,231 A | 10/1983 | Stenzel et al. |
| 4,985,352 A | 1/1991 | Julius et al. |
| 5,077,409 A | 12/1991 | Wissner |
| 5,128,351 A | 7/1992 | Wissner |
| 5,523,280 A | 6/1996 | Chene et al. |
| 5,661,024 A | 8/1997 | Kao et al. |
| 5,712,279 A | 1/1998 | Biller et al. |
| 5,739,135 A | 4/1998 | Biller et al. |
| 5,760,246 A | 6/1998 | Biller et al. |
| 5,886,044 A | 3/1999 | Widdowson et al. |
| 5,905,080 A | 5/1999 | Duckworth et al. |
| 5,945,382 A | 8/1999 | Cantegril et al. |
| 5,990,133 A | 11/1999 | Gaster et al. |
| 6,005,008 A | 12/1999 | Widdowson et al. |
| 6,028,085 A | 2/2000 | Bromibge |
| 6,054,472 A | 4/2000 | Armistead et al. |
| 6,140,509 A | 10/2000 | Behan et al. |
| 6,271,261 B1 | 8/2001 | Widdowson |
| 6,297,261 B1 | 10/2001 | Christophersen et al. |
| 6,417,393 B1 | 7/2002 | Christophersen et al. |
| 6,479,480 B1 | 11/2002 | Moyes et al. |
| 6,479,519 B1 | 11/2002 | Astles et al. |
| 6,531,291 B1 | 3/2003 | Kabbash et al. |
| 6,541,209 B1 | 4/2003 | Behan et al. |
| 6,696,475 B2 | 2/2004 | Dahl et al. |
| 6,706,749 B2 | 3/2004 | Dahl et al. |
| 6,784,183 B2 | 8/2004 | Lavielle et al. |
| 7,884,101 B2 | 2/2011 | Teegarden et al. |
| 8,148,417 B2 | 4/2012 | Teegarden et al. |
| 2002/0025965 A1 | 2/2002 | Lavielle et al. |
| 2004/0102636 A1 | 5/2004 | Miller et al. |
| 2005/0054691 A1 | 3/2005 | Potter et al. |
| 2005/0080124 A1 | 4/2005 | Teegarden et al. |
| 2005/0267097 A1 | 12/2005 | Pinto et al. |
| 2006/0014705 A1 | 1/2006 | Howitz et al. |
| 2006/0063754 A1 | 3/2006 | Edgar et al. |
| 2006/0205792 A1 | 9/2006 | Wong et al. |
| 2006/0229335 A1 | 10/2006 | Teegarden et al. |
| 2007/0037827 A1 | 2/2007 | Nunes et al. |
| 2007/0072857 A1 | 3/2007 | Teegarden et al. |
| 2007/0207994 A1 | 9/2007 | Teegarden et al. |
| 2007/0244086 A1 | 10/2007 | Teegarden et al. |
| 2008/0015223 A1 | 1/2008 | Strah-Pleynet et al. |
| 2008/0200530 A1 | 8/2008 | Unett et al. |
| 2009/0186895 A1 | 7/2009 | Teegarden et al. |
| 2009/0189935 A1 | 7/2009 | Kunimatsu |
| 2009/0197935 A1 | 8/2009 | Teegarden et al. |

FOREIGN PATENT DOCUMENTS

| EP | 1108720 | 6/2001 |
|---|---|---|
| EP | 1558582 | 8/2005 |

(Continued)

OTHER PUBLICATIONS

Adams et al., "APD791, a Novel 5-HT2A Receptor Antagonist: Pharmacological Profile, Pharmacokinetics, Platelet and Vascular Biology," JPET # 153189, published on Jul. 23, 2009, 38 pages.

(Continued)

*Primary Examiner* — Rebecca Anderson
*Assistant Examiner* — Alicia L Otton

(57) ABSTRACT

The present invention relates to processes for preparing phenyl-pyrazoles of Formula (I) and salts and pharmaceutical compositions thereof, useful as modulators of 5-HT$_{2A}$ serotonin receptor activity. The present invention also relates to intermediates used in the processes, and their preparation. The present invention also relates to crystalline forms of 5-HT$_{2A}$ serotonin receptor modulators, compositions thereof and methods of using the same.

32 Claims, 8 Drawing Sheets

FOREIGN PATENT DOCUMENTS

| | | |
|---|---|---|
| EP | 1734039 | 12/2006 |
| WO | WO 96/02138 | 2/1996 |
| WO | WO 96/10559 | 4/1996 |
| WO | WO 97/03967 | 2/1997 |
| WO | WO 97/45111 | 12/1997 |
| WO | WO 98/24785 | 6/1998 |
| WO | WO 99/06354 | 2/1999 |
| WO | WO 99/32436 | 7/1999 |
| WO | WO 99/32463 | 7/1999 |
| WO | WO 99/52927 | 10/1999 |
| WO | WO-00/57877 | 5/2000 |
| WO | WO 00/57877 | 10/2000 |
| WO | WO 00/64866 | 11/2000 |
| WO | WO 01/21160 | 3/2001 |
| WO | WO 01/29008 | 4/2001 |
| WO | WO 02/39987 | 5/2002 |
| WO | WO-02/39987 A2 | 5/2002 |
| WO | WO 02/051833 | 7/2002 |
| WO | WO 02/076464 | 10/2002 |
| WO | WO 03/062206 | 7/2003 |
| WO | WO 2004/028450 | 4/2004 |
| WO | WO-2004/045118 A2 | 5/2004 |
| WO | WO 2004/058722 | 7/2004 |
| WO | WO 2004/071426 | 8/2004 |
| WO | WO 2004/085433 | 10/2004 |
| WO | WO 2004/096771 | 11/2004 |
| WO | WO 2005/012254 | 2/2005 |
| WO | WO 2005/077345 | 8/2005 |
| WO | WO 2005/103011 | 11/2005 |
| WO | WO 2006/018662 | 2/2006 |
| WO | WO 2006/049734 | 5/2006 |
| WO | WO 2006/049941 | 5/2006 |
| WO | WO 2006/055734 | 5/2006 |
| WO | WO 2006/059149 | 6/2006 |
| WO | WO 2006/060654 | 6/2006 |
| WO | WO 2006/070394 | 7/2006 |
| WO | WO 2006/076592 | 7/2006 |
| WO | WO 2006/078610 | 7/2006 |
| WO | WO 2006/079637 | 8/2006 |
| WO | WO 2006/081335 | 8/2006 |
| WO | WO 2006/086705 | 8/2006 |
| WO | WO 2006/089871 | 8/2006 |
| WO | WO 2006/095205 | 9/2006 |
| WO | WO 2006/097766 | 9/2006 |
| WO | WO 2006/100519 | 9/2006 |
| WO | WO 2006/112464 | 10/2006 |
| WO | WO 2006/116614 | 11/2006 |
| WO | WO 2007/002559 | 1/2007 |
| WO | WO 2007/026959 | 3/2007 |
| WO | WO 2007/120600 | 10/2007 |
| WO | WO 2007/129111 | 11/2007 |
| WO | WO 2007/136680 | 11/2007 |
| WO | WO-2007/136689 A2 | 11/2007 |
| WO | WO 2007/136703 | 11/2007 |
| WO | WO 2007/136875 | 11/2007 |
| WO | WO 2008/027483 | 3/2008 |
| WO | WO 2008/042388 | 4/2008 |
| WO | WO 2008/054748 | 5/2008 |
| WO | WO 2009/023253 | 2/2009 |
| WO | WO2011/075596 A1 | 6/2011 |
| WO | WO-2011-075596 A1 | 6/2011 |

OTHER PUBLICATIONS

Advisory Action dated Sep. 9, 2009 from U.S. Appl. No. 11/602,164.

Antinori et al, "Diagnosis of AIDS-related focal brain lesions: a decision-making analysis based on clinical and neuroradiologic characteristics combined with polymerase chain reaction assays in CSF," Neurology, 48:687-694 (1997).

Berger et al., "Progressive multifocal leukoencephalopathy," Seminars in Neurology, 19:193-200 (1999).

Burger, A. "Isosterism and bioisosterism in drug design," Prog. Drug Res. , 37: 287-371 (1991).

Chang, C. et al. "Ipsapirone and ketanserin protects against circulatory shock, intracranial hypertension, and cerebral ischemia during heatstroke," Shock 24(4): 336-340 (2005).

Deuchar, G. et al. "The role of 5-hydroxytryptamine in the control of pulmonary vascular tone in a rabbit model of pulmonary hypertension secondary to left ventricular dysfunction," Pulm. Pharmacol. Ther. 18(1):23-31(2005).

Final Office Action dated Jan. 2, 2009 from U.S. Appl. No. 11/602,164.

Final Office Action dated Jun. 19, 2009 from U.S. Appl. No. 11/602,164.

Fujita et al., "Sarpogrelate treatment reduces restenosis after coronary stenting," Am Heart Journal, 145:16 (2003).

Fujiwara et al., "Augmented responses to 5-HT2-receptor-mediated vasoconstrictions in atherosclerotic rabbit common carotid arteries," Journal of Cardiovascular Pharmacology, 26:503-510, (1995).

Hayashi, T. et al. "Sarpogrelate HCl, a selective 5-HT2A antagonist, retards the progression of atherosclerosis through a novel mechanism," Atherosclerosis 168: 23-31 (2003).

Hong et al., "Topical ketanserin attenuates hyeralgesia and inflammation in arthritis in rats," Pain 124, pp. 27-33 (2006).

Horibe, E., "Sarpogrelate, a 5-HT2 receptor blocker, may have a preconditioning-like effect in patients with coronary artery disease," Circulation Research 68:68-72, 15 (2004).

International Search Report for International Application No. PCT/US2005/011789, dated Oct. 28, 2005.

International Search Report for International Application No. PCT/US2007/0011834, dated Feb. 10, 2007 by Authorized Officer Bart De Jong.

International Search Report for International Application No. PCT/US2007/011789, dated Nov. 2, 2007.

International Search Report for International Application No. PCT/US2007/011834, dated Oct. 2, 2007 by Authorized Officer Bart De Jong.

Krieger et al., "Novel immunosuppressants," Pediatr Transplantation, 8:594-599 (2004).

Major et al., "Establishment of a line of human fetal glial cells that supports JC virus multiplication," PNAS USA, , 82:1257-1261 (1985).

Marcos et al., "Serotonin-induced smooth muscle hyperplasia in various forms of human pulmonary hypertension," Circ. Res. 94(9): 1263-70 (2004).

Miao, C. et al. "Ketanserin stabilizes blood pressure in conscious spontaneously hypertensive rats," Clin. Exp. Pharmacol. Physio. 30(3):189-193, (2003).

Mueller, "Drug immunosuppression therapy for adult heart transplantation. Part 1: immune response to allograft and mechanism of action of immunosuppressants," Ann Thorac Surg. 77:354-362 (2004).

Nakajima et al., "The nociceptive mechanism of 5-hydroxtryptamine released into the peripheral tissue in acute inflammatory pain in rats," European Journal of Pain 13, pp. 441-447 (2009).

Nitanda et al., "Contribution of the peripheral 5-$HT_{2A}$ receptor to mechanical hyperalgesia in a rat model of neuropathic pain," Neurochemistry International 47, pp. 394-400 (2005).

Non Final Office Action dated Jul. 23, 2008 from U.S. Appl. No. 11/602,164.

Notice of Allowance dated Sep. 27, 2010 from U.S. Appl. No. 11/602,164.

Office Action dated Jan. 2, 2009 from U.S. Appl. No. 11/602,164.
Office Action dated Jul. 23, 2008 from U.S. Appl. No. 11/602,164.
Office Action dated Jun. 19, 2009 from U.S. Appl. No. 11/602,164.

Pawlak D. et al., "A potent 5-hydroxytryptamine receptor (5-HT2A) antagonist, DV-7028, delays arterial thrombosis development in rats," Thrombosis Research 90: 259-270 (1998).

Portegies et al., "Guidelines for the diagnosis and management of neurological complications of HIV infection," Eur. J. Neurol. 11:297-304 (2004).

Querbes et al., "A JC virus-induced signal is required for infection of glial cells by a clathrin- and eps15-dependent pathway," J Virology, 78:250-256 (2004).

Restriction Requirement dated Apr. 7, 2008 from U.S. Appl. No. 11/597,306.

Restriction Requirement dated Feb. 14, 2011 from U.S. Appl. No. 12/301,172.

Restriction Requirement dated Feb. 14, 2011 from U.S. Appl. No. 12/301,180.

Restriction Requirement dated Jan. 24, 2008 from U.S. Appl. No. 11/602,164.
Restriction Requirement dated Mar. 14, 2011 from U.S. Appl. No. 12/976,887.
Silva, A., Chronic treatment with mianserin prevents DOCA-salt hypertension in rats—evidence for the involvement of central 5-HT2 receptors, Eur J. Pharmacol. 518(2-3): 152-172 (2005).
Singh et al., "Immunosuppressive-associated leukoencephalopathy in organ transplant recipients," Transplantation, 69:467-472 (2000).
Stella, V. "Pro-drugs as Novel Drug Delivery Systems", Higuchi, T. et al., ed. (American Chemical Society, Washington), pp. 1-49 (1975).
Stenzel et al., Document No. 94:208858, 1981, retrieved from CAPLUS.
Topliss, J.G., "A Manual Method for Applying the Hansch Approach to Drug Design," J. Med. Chem. 20(4), pp. 463-469. (1977).
Turpin, "The next generation of HIV/AIDS drugs: novel and developmental antiHIV drugs and targets," Expert Rev Anti Infect Ther. Jun. 1(1):97-128 (2003).
Vacante et al., "Extension of JC virus host range to monkey cells by insertion of a simian virus 40 enhancer into the JC virus regulatory region," Virology, 170:353-361, (1989).
Yamada et al., "Phase I/II trial of didanosine (2',3'-dideoxyinosine) in hemophiliac patients with AIDS or AIDS-related complex," Clin. Diag. Virol. 1:245-256 (1993).
Yamashita et al., "Conjunctive effects of the 5HT(2) receptor antagonist, sarpogrelate, on thrombolysis with modified tissue plasminogen activator in different laser-induced thrombosis models," Haemostasis, 30:321-332, (2000).
American Academy of Sleep Medicine, "The International Classification of Sleep Disorders, Revised," 2001.
Andrezejewska-Buczko, J. et al., "Serotonin in diabetic retinopathy," Klinika Oczna, 98(2):101-4 (1996) Abstract.
Berge, S. et al., "Pharmaceutical salts," Journal of Pharmaceutical Sciences, 66(1):1-19 (1977).
Blier, P. et al., "Putative mechanisms of action of antidepressant drugs in affective and anxiety disorders and pain," Journal of Psychiatry and Neuroscience, 26(1):37-43 (2000).
Cameron, N. at al., "The effects of 5-hydroxytryptamine 5-$HT_2$ receptor antagonists on nerve conduction velocity and endoneurial perfusion in diabetic rats," Naunyn Schmiedeberg's Archive of Pharmacology, 367:607-14 (2003).
Casey, C. et al., "Constitutively active mutant $5HT_{2A}$ serotonin receptors: inverse agonist activity of classical $5HT_{2A}$ antagonists," Society for Neuroscience, 22:1778 (1996) Abstract.
Catalán, J. et al., "New Ultraviolet Stabilizers: 3- and 5-(2'-Hydroxyphenyl)pyrazoles," J. Am. Chem. Soc., 114, 5039-5048 (1992).
Cazzola, M. et al., "5-HT modifiers as a potential treatment of asthma," TiPS, 21:13-6 (2000).
Chang, F. W. et al., "Mechanism of ocular hypotensive action of ketanserin," Journal of Ocular Pharmacology, 1(2):137-47 (1985).
Cohen-Mansfield, J. et al., "Agitated behaviors in the elderly I. A conceptual review," JAGS, 34(10):711-21 (1986).
Collier, T. L. et al., "Radiosynthesis and in vivo evaluation of the psuedopeptide δ-opioid antagonist [$^{125}$I]-ITIPP($\psi$)," Journal of Labelled Cpd. Radiopharm., 42 (Suppl. 1):S264-6 (1999).
De Bie, J. J. et al., "Modulation of airway hyperresponsiveness and eosinophilia by selective histamine and 5-HT receptor antagonists in a mouse model of allergic asthma," British Journal of Pharmacology, 124:857-64 (1998).
Elliott, J. M. et al., "4-Oxospiro[benzopyran-2,4'-piperidines] as Class III Antiarrhythmic Agents. Pharmacological Studies on 3,4-Dihydro-1'-[2-(benzofurazan-5-yl)-ethyl]-6methanesulfonamidospiro[(2H)-1-benzopyran-2,4'-piperidini]-4-one (L-691,121)", J. Med. Chem., 35:3973-3976 (1992).
Elphick, G. et al., "The human polyomavirus, JCV, uses serotonin to infect cells," Science, 306:1380-3 (2004).
Greene et al., Protective Groups in Organic Synthesis, 3$^{rd}$ Edition, 1999 (Wiley).
Gründer, G. et al., "Time course of 5-$HT_{2A}$ receptor occupancy in the human brain after a single dose of the putative antipsychotic drug MDL 100,907 measured by positron emission tomography," Neuropsychopharmacology, 17(3):175-85 (1997).

Herrick-Davis, K. et al., "Constitutively active 5HT2C serotonin receptor created by site directed mutagenesis," Society for Neuroscience, 22:1779 (1996) Abstract.
Herrick-Davis, K. et al., "Activating mutations of the serotonin $5HT_{2c}$ receptor," Journal of Neurochemistry, 69(3):1138-44 (1997).
Higuchi et al., "Pro-Drugs and Novel Delivery Systems", vol. 14 of the ACS Symposium Series; and in Bioreversible Carriers in Drug Design, ed. Edward B. Roche, American Pharmaceutical Association and Pergamon Press, 1987.
Kanayama, M. et al., "New treatment of lumbar disc herniation using 5-hydroxytryptamine$_{2A}$ receptor inhibitor: a randomized controlled trial," Journal of Neurosurgery: Spine, 2:441-6 (2005).
Katz, I. et al., "Comparison of risperidone and placebo for psychosis and behavioral disturbances associated with dementia: a randomized double-blind trial," Journal of Clinical Psychiatry, 60(2): 107-15 (1999).
Kitagawa, O. et al., "Beckmann Rearrangement of O-4 Pentenyl Oxime through N-Bromosuccinimide-Mediated Activating Process", Chem. Pharm. Bull., 45(1) 32-35 (1997).
Koss, E. et al., "Assessing patterns of agitation in Alzheimer's disease patients with the Cohen-Mansfield agitation inventory," Alzheimer's Disease and Associated Disorders, 11(S2):S45-50 (1997).
Landolt, H. et al., "Serotonin-2 receptors and human sleep: effect of a selective antagonist on EEG power spectra," Neuropsychopharmacology, 21(3):455-66 (1999).
Le Bas, M. et al., "Radioiodinated analogs of EP 00652218 for the exploration of the tachykinin NK1 receptor by spect," Journal of Labelled Cpd. Radiopharm., 44(S1):S280-2 (2001).
Mastropasqua, L. et al., "Ocular hypotensive effect of ketanserin in patients with primary open angle glaucoma," Acta Ophthalmologica Scandinavica, 75:24-5 (1997).
Muto, T. et al., "Protective effects of sarpogrelate, a $5HT_{2A}$ antagonist, against postischemic myocardial dysfunction in guinea-pig hearts," Molecular and Cellular Biochemistry, 272:119-32 (2005).
National Institutes of Health, "Facts about Insomnia," NIH publication No. 95-3801 (1995).
Nishiyama, T., "Effects of $5HT_{2A}$ receptor antagonist, sarpogrelate on thermal or inflammatory pain," European Journal of Pharmacology, 516:18-22 (2005).
Nomura, S. et al., "$5HT_{2A}$ receptor antagonist increases circulating adiponectin in patients with type 2 diabetes," Blood Coagulation and Fibrinolysis, 16(6):423-8 (2005).
Pietraszek, M. H. et al., "Blood serotonergic mechanisms in type 2 (non-insulin dependant) diabetes mellitus," Thrombosis Research, 66:765-74 (1992).
Remington, The Science and Practice of Pharmacy, 20$^{th}$ Edition, 2000 (Lippincott Williams & Wilkins).
Satomura, K. et al., "Sarpogrelate, a specific 5HT2-receptor antagonist, improves the coronary microcirculation in coronary artery disease," Clinical Cardiology, 25:28-32 (2002).
Sawnyok, J. et at, "Antidepressants as analgesics: an overview of central and peripheral mechanisms of action," Journal of Psychiatry and Neuroscience, 26(1):21-9 (2001).
Sharpley, A.L. et al., "Slow wave sleep in humans: role of $5HT_{2A}$ and $5HT_{2C}$ receptors," Neuropharmacology, 33(3/4):467-71 (1994).
Smith, G. et al., "Test-retest variability of serotonin $5HT_{2A}$ receptor binding measured with positron emission tomography and [$^{18}$F]altanserin in the human brain," Synapse, 30:380-92 (1998).
Staley, J. et al., "Comparison of [$^{18}$F]altanserin and [$^{18}$F]deuteroaltanserin for PET imaging of serotonin$_{2A}$ receptors in baboon brain: pharmacological studies," Nuclear Medicine and Biology, 28:271-9 (2001).
Strah-Pleynet, S. et al., "Discovery and SAR of novel $5HT_{2A}$ inverse-agonists," 227$^{th}$ ACS National Meeting, MEDI 270 (2004).
Street, J. et al., "Olanzapine treatment of psychotic and behavioral symptoms in patients with Alzheimer disease in nursing care facilities," Archive of General Psychiatry, 57:968-76 (2000).
Takahashi, T. et al., "Sarpogrelate hydrochloride, a serotonin 2A receptor antagonist, reduces albuminuria in patients with early-stage diabetic nephropathy," Diabetes Research and Clinical Pratice, 58:123-9 (2002).

Takenaka, H. et al., "The effect of Anplag® (sarpogrelate HCL). Novel selective 5-HT$_2$ antagonist of intraocular pressure in glaucoma patients," *Investigative Ophthalmology & Visual Science*, 36(4):S734 (1995) Abstract.

Talvik-Lofti, M. et al., "High 5HT$_{2A}$ receptor occupancy in M100907-treated schizophrenic patients," *Psychopharmacology*, 148:400-3 (2000).

The International Classification of Sleep Disorders, Revised Diagnostic and Coding Manual, American Academy of Sleep Medicine (2001) pp. 1-336 (also includes table of contents and glossary).

Verstraete, M. "Prevention of atherosclerotic complications: controlled trial of ketanserin," *British Medical Journal*, 298:424-30 (1989).

Vikenes, K. et al., "Serotonin is associated with coronary artery disease and cardiac events," Circulation, 100:483-9 (1999).

Vippagunta, S. et al., "Crystalline solids," *Advanced Drug Delivery Reviews*, 48:3-26 (2001).

Wilson, H et al., "LY53857, a 5HT$_2$ receptor antagonist, delays occlusion and inhibits platelet aggregation in a rabbit model of carotid artery occlusion," *Thrombosis and Haemostasis*, 66 (3) 355-60 (1991).

Winokur, A. et al., "Acute effects of Mirtazapine on sleep continuity and sleep architecture in depressed patients: a pilot study," *Biological Psychiatry*, 48:75-8 (2000).

Zhu, G. et al., "Synthesis and mode of action of $^{125}$I- and $^3$H-labeled thieno[2,3,-c]pyridine antagonists of cell adhesion molecule expression," *Journal of Organic Chemistry*, 67:943-8 (2002).

International Search Report for International Application No. PCT/US2005/041726 dated May 18, 2006 by Authorized Officer Stefan Härtinger.

International Search Report for International Application No. PCT/US2007/011810 dated Oct. 30, 2007 by Authorized Officer Bart De Jong.

International Preliminary Report on Patentability for International Application No. PCT/US2005/041726 dated Sep. 21, 2006 by Authorized Officer Stefan Härtinger.

International Preliminary Report on Patentability for International Application No. PCT/US2007/011810 dated Jul. 16, 2008 by Authorized Officer Bart De Jong.

Dosa, et al., Synthesis and SAR of Solubilized Pyrazole Derivatives as 5-HT$_{2A}$ Inverse-Agonists for Platelet Aggregation. 232$^{nd}$ ACS National Meeting (Sep. 2006).

U.S. Appl. No. 12/301,172, Office Action dated Jul. 27, 2011.

U.S. Appl. No. 12/301,172, Notice of Allowance dated Nov. 22, 2011.

U.S. Appl. No. 12/301,180, Office Action dated Jul. 27, 2011.

U.S. Appl. No. 12/301,180, Notice of Allowance dated Nov. 28, 2011.

U.S. Appl. No. 12/976,887, Office Action dated Sep. 7, 2011.

U.S. Appl. No. 12/976,887, Office Action dated Feb. 15, 2012.

U.S. Appl. No. 12/976,887, Advisory Action dated May 1, 2012.

Prosser, et al. "Selective serotonin 5-HT2A inverse agonists promote sleep consolidation in male Wistar rats during the normal inactive phase." #29, Arena Pharmaceuticals, SRI Intl (2004).

Shibata et al., "Adiponectin protects against myocardial ischemia-reperfusion injury through AMPK- and COX-2-dependent mechanisms." Nature Medicine, Advance Online Publication (Sep. 11, 2005).

STN Abstract for WO2003/062206, Jul. 31, 2003.

4-(2-(4-(3-Methoxybenzamido)-2-(1-methyl-1H-pyrazol-5-yl)phenoxy)ethyl)morpholin-4-ium Chloride Form I Thermogravimetric Analysis (TGA)

4-(2-(4-(3-Methoxybenzamido)-2-(1-methyl-1H-pyrazol-5-yl)phenoxy)ethyl)morpholin-4-ium chloride Form I
Digital Scanning Calorimetry (DSC)

4-(2-(4-(3-Methoxybenzamido)-2-(1-methyl-1H-pyrazol-5-yl)phenoxy)ethyl)morpholin-4-ium Chloride Form I 4-(2-(4-(3-Methoxybenzamido)-2-(1-methyl-1*H*-pyrazol-5-yl)phenoxy)ethyl)morpholin-4-ium Chloride Form I Dynamic Vapor Sorption (DVS)

Adsorption/Desorption Isotherm

4-Acetyl-1-(2-(4-(3-fluorobenzamido)-2-(1-methyl-1H-pyrazol-5-yl)
phenoxy)ethyl)piperazin-1-ium Carboxyformate Form I
Thermogravimetric Analysis (TGA)

4-Acetyl-1-(2-(4-(3-fluorobenzamido)-2-(1-methyl-1*H*-pyrazol-5-yl)
phenoxy)ethyl)piperazin-1-ium Carboxyformate Form I
Digital Scanning Calorimetry (DSC)

4-Acetyl-1-(2-(4-(3-fluorobenzamido)-2-(1-methyl-1H-pyrazol-5-yl phenoxy)ethyl)piperazin-1-ium Carboxyformate Form 1

Powder X-Ray Diffraction (PXRD)

4-Acetyl-1-(2-(4-(3-fluorobenzamido)-2-(1-methyl-1H-pyrazol-5-yl)phenoxy)ethyl)piperazin-1-ium Carboxyformate Form I

CRYSTALLINE FORMS AND PROCESSES FOR THE PREPARATION OF PHENYL-PYRAZOLES USEFUL AS MODULATORS OF THE 5-HT$_{2A}$ SEROTONIN RECEPTOR

FIELD OF THE INVENTION

The present invention relates to processes for preparing phenyl-pyrazoles of Formula (I) and salts and pharmaceutical compositions thereof, useful as modulators of 5-HT$_{2A}$ serotonin receptor activity. The present invention also relates to intermediates used in the processes, and their preparation. The present invention also relates to crystalline forms of 5-HT$_{2A}$ serotonin receptor modulators, compositions thereof and methods of using the same.

BACKGROUND OF THE INVENTION

Receptors for serotonin (5-hydroxytryptamine, 5-HT) are an important class of G protein coupled receptors. Serotonin receptors are divided into seven subfamilies, referred to as 5-HT$_1$ through 5-HT$_7$, inclusive. These subfamilies are further divided into subtypes. For example, the 5-HT$_2$ subfamily is divided into three receptor subtypes: 5-HT$_{2A}$, 5-HT$_{2B}$, and 5-HT$_{2C}$. Certain phenyl-pyrazoles are modulators of 5-HT$_{2A}$ serotonin receptor activity useful in the treatment of platelet aggregation, coronary artery disease, myocardial infarction, transient ischemic attack, angina, stroke, atrial fibrillation, blood clot formation, asthma or symptoms thereof, agitation or a symptom thereof, behavioral disorders, drug induced psychosis, excitative psychosis, Gilles de la Tourette's syndrome, manic disorder, organic or NOS psychosis, psychotic disorder, psychosis, acute schizophrenia, chronic schizophrenia, NOS schizophrenia and related disorders, sleep disorders, diabetic-related disorders, progressive multifocal leukoencephalopathy, and the like.

Because drug compounds having, for example, improved stability, solubility, shelf life, and in vivo pharmacology, are consistently sought, there is an ongoing need for new or purer salts, hydrates, solvates, and polymorphic crystalline forms of existing drug molecules. The crystalline form of 4-(2-(4-(3-methoxybenzamido)-2-(1-methyl-1H-pyrazol-5-yl)phenoxy)ethyl)morpholin-4-ium chloride, designated as Form I, and the crystalline form of 4-acetyl-1-(2-(4-(3-fluorobenzamido)-2-(1-methyl-1H-pyrazol-5-yl)phenoxy)ethyl)piperazin-1-ium carboxyformate, designated as Form I, described herein help meet this and other needs.

SUMMARY OF THE INVENTION

Figure 1:
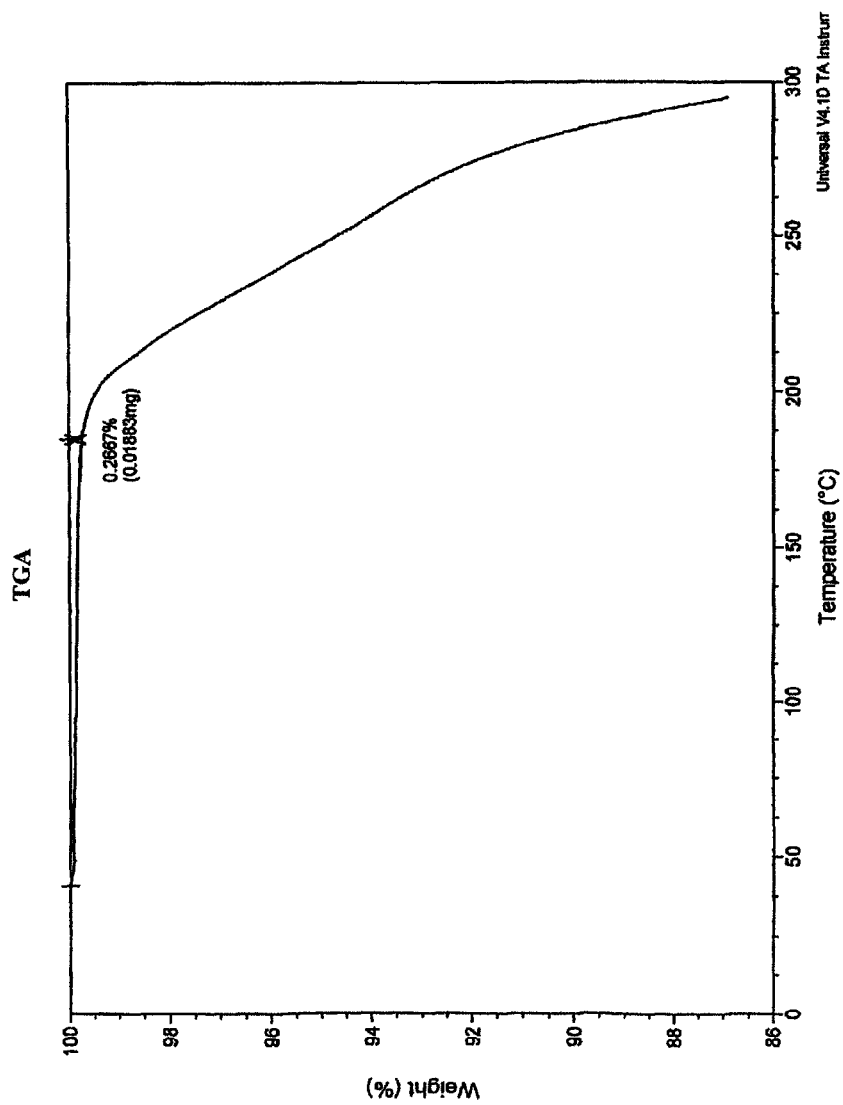
FIG. 1 depicts a thermogravimetric analysis (TGA) thermogram for crystalline Form I of Compound 7 of the invention (TA Instruments TGA Q500 in open cell; 25-300° C.; 10° C./min).

The present invention provides, inter alia, processes for preparing compounds of Formula (I):

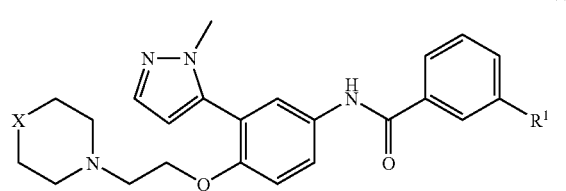

(I)

or a salt form thereof,
wherein:
 R$^1$ is C$_1$-C$_8$ alkyl, halo, C$_1$-C$_8$ haloalkyl or C$_1$-C$_8$ alkoxy;
 X is O, S, NR$^2$ or CHR$^2$; and
 R$^2$ is H, C$_1$-C$_8$ alkyl, C$_1$-C$_8$ acyl, C$_1$-C$_8$ alkenyl, C$_1$-C$_8$ alkynyl, C$_3$-C$_7$ cycloalkyl, C$_1$-C$_8$ haloalkyl, arylalkyl, aryl, heteroaryl or heteroarylalkyl each optionally substituted with C$_1$-C$_8$ alkyl, halo, C$_1$-C$_8$ haloalkyl or C$_1$-C$_8$ alkoxy;

comprising reacting a compound of Formula (II):

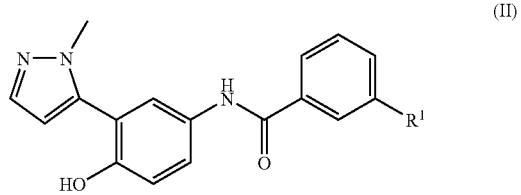

(II)

with a compound of Formula (III):

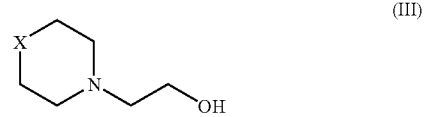

(III)

in the presence of a trisubstituted phosphine and a compound having the Formula (A):

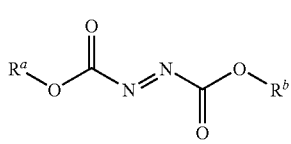
(A)

wherein:
  $R^a$ and $R^b$ are each, independently, $C_1$-$C_{10}$ alkyl or $C_1$-$C_7$ cycloalkyl; to form a compound of Formula (I).

The present invention further provides processes for preparing compounds of Formula (II) comprising reacting a compound of Formula (IV):

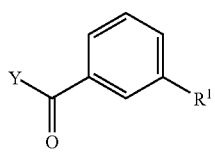
(IV)

wherein:
  Y is halo, OH or $OC(O)R^3$; and
  $R^3$ is $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, arylalkyl, aryl, heteroaryl or heteroarylalkyl each optionally substituted with $C_1$-$C_8$ alkyl, halo, $C_1$-$C_8$ haloalkyl or $C_1$-$C_8$ alkoxy;
with a compound of Formula (V):

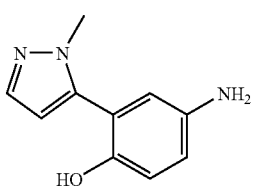
(V)

or a salt thereof to form a compound of Formula (II).

The present invention further provides processes for preparing a compound of Formula (V) or a salt thereof comprising reacting a compound of Formula (VI):

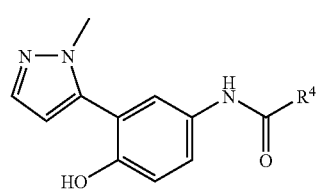
(VI)

wherein:
  $R^4$ is $C_1$-$C_8$ alkyl, $C_1$-$C_8$ alkenyl, $C_1$-$C_8$ alkynyl, $C_3$-$C_7$ cycloalkyl, arylalkyl, aryl, heteroaryl or heteroarylalkyl each optionally substituted with $C_1$-$C_8$ alkyl;
with a cleaving reagent to form a compound of Formula (V) or a salt thereof.

The present invention further provides processes for preparing compounds of Formula (VI) comprising reacting a compound of Formula (VII):

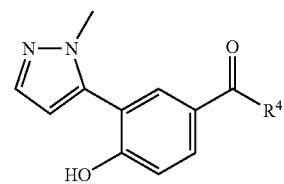
(VII)

with an amine in the presence of an acid to form a compound of Formula (VI).

The present invention further provides processes for preparing compounds of Formula (VII) comprising reacting a compound of Formula (IX):

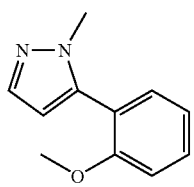
(IX)

with a compound of the Formula (X):

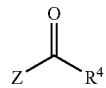
(X)

wherein:
  Z is halo or $OC(O)R^5$;
  $R^5$ is $C_1$-$C_8$ alkyl, $C_1$-$C_8$ acyl, $C_1$-$C_8$ alkenyl, $C_1$-$C_8$ alkynyl, $C_3$-$C_7$ cycloalkyl, arylalkyl, aryl, heteroaryl or heteroarylalkyl each optionally substituted with $C_1$-$C_8$ alkyl;
in the presence of a Lewis acid to form a compound of Formula (VII).

The present invention further provides processes for preparing compounds of Formula (VI) comprising reacting a compound of Formula (VIII):

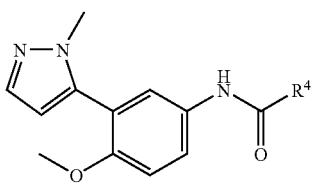
(VIII)

with a demethylating agent to form a compound of Formula (VI).

The present invention further provides processes for preparing compounds of Formula (VIII) comprising reacting a compound of Formula (IX):

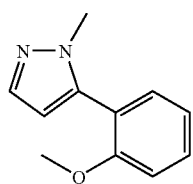

(IX)

with a compound of Formula (XI):

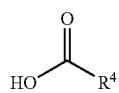

(XI)

and an amine to form a compound of Formula (VIII).

The present invention further provides processes for preparing a compound of Formula (VI) comprising reacting a compound of Formula (XIV):

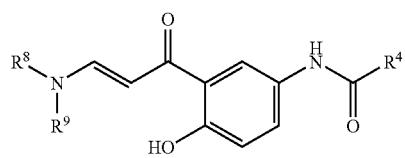

(XIV)

wherein:

$R^8$ and $R^9$ are each independently $C_1$-$C_8$ alkyl or arylalkyl; or $R^8$ and $R^9$ together with the nitrogen atom to which they are both bonded form a heterocyclyl or a heterobicyclyl group; with methyl hydrazine in the presence of a catalyst to form said compound of Formula (VI).

The present invention further provides processes for preparing a compound of Formula (XIV) comprising reacting a compound of Formula (XV):

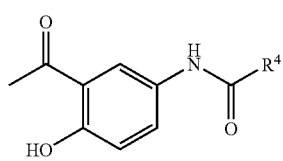

(XV)

with a compound of Formula (XVI):

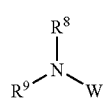

(XVI)

wherein:

W is formyl or —CH(OR$^{10}$)(OR$^{11}$);

and $R^{10}$ and $R^{11}$ are each independently $C_1$-$C_8$ alkyl; to form said compound of Formula (XIV).

The present invention further provides processes for preparing salts of compounds of Formula (I):

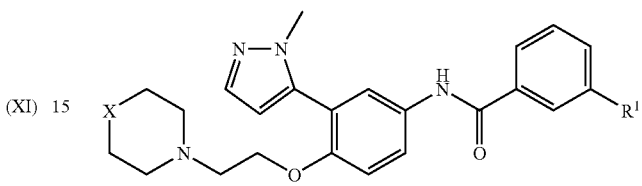

(I)

comprising reacting a compound of Formula (I) with a salt-forming acid to form a salt of a compound of Formula (I).

The present invention further provides salts of compounds of Formula (I) prepared by the processes described herein.

The present invention further provides pharmaceutical compositions of compounds of Formula (I) prepared by the processes described herein.

The present invention further provides compounds of Formula (II), Formula (V) and Formula (VII) prepared by the processes described herein.

In some embodiments, the present invention provides 4-(2-(4-(3-methoxybenzamido)-2-(1-methyl-1H-pyrazol-5-yl)phenoxy)ethyl)morpholin-4-ium chloride.

In some embodiments, the present invention provides (4-(2-(4-(3-methoxybenzamido)-2-(1-methyl-1H-pyrazol-5-yl)phenoxy)ethyl)morpholin-4-ium chloride having crystalline form I.

In some embodiments, the present invention provides 4-acetyl-1-(2-(4-(3-fluorobenzamido)-2-(1-methyl-1H-pyrazol-5-yl)phenoxy)ethyl)piperazin-1-ium carboxyformate.

In some embodiments, the present invention provides 4-acetyl-1-(2-(4-(3-fluorobenzamido)-2-(1-methyl-1H-pyrazol-5-yl)phenoxy)ethyl)piperazin-1-ium carboxyformate having crystalline form I.

In some embodiments, the present invention provides compositions comprising a crystalline form of the invention.

In some embodiments, the present invention provides compositions comprising a crystalline form of the invention and a pharmaceutically acceptable carrier.

In some embodiments, the present invention provides processes for preparing a crystalline form of the invention as well as a crystalline form prepared by the processes.

In some embodiments, the present invention provides methods for modulating a 5HT$_{2A}$ receptor comprising contacting said receptor with a salt or a crystalline form as described herein.

In some embodiments, the present invention provides methods for treating a 5HT$_{2A}$-related disorder comprising administering to a patient in need thereof a therapeutically effective amount of a salt or a crystalline form as described herein.

In some embodiments, the present invention provides methods of treating platelet aggregation, coronary artery disease, myocardial infarction, transient ischemic attack, angina, stroke, atrial fibrillation, blood clot formation, asthma or symptoms thereof, agitation or a symptom thereof, behavioral disorders, drug induced psychosis, excitative psychosis, Gilles de la Tourette's syndrome, manic disorder, organic or NOS psychosis, psychotic disorder, psychosis, acute schizophrenia, chronic schizophrenia, NOS schizophrenia and related disorders, sleep disorders, diabetic-related disorders, progressive multifocal leukoencephalopathy by administering to a patient in need thereof a therapeutically effective amount of a salt or a crystalline form as described herein.

In some embodiments, the present invention provides methods of treating coronary artery disease, myocardial infarction, transient ischemic attack, angina, stroke, and atrial fibrillation comprising administering to a patient in need thereof a therapeutically effective amount of a salt or a crystalline form as described herein.

In some embodiments, the present invention provides methods of treating a condition associated with platelet aggregation comprising administering to a patient in need thereof a therapeutically effective amount of a salt or a crystalline form as described herein.

In some embodiments, the present invention provides methods of reducing the risk of blood clot formation in an angioplasty or coronary bypass surgery individual comprising administering to a patient in need thereof a therapeutically effective amount of a salt or a crystalline form as described herein.

In some embodiments, the present invention provides methods of reducing the risk of blood clot formation in an individual suffering from atrial fibrillation comprising administering to a patient in need thereof a therapeutically effective amount of a salt or a crystalline form as described herein.

In some embodiments, the present invention provides methods of treating a sleep disorder comprising administering to a patient a therapeutically effective amount of a salt or a crystalline form as described herein.

In some embodiments, the present invention provides methods of treating a dyssomnia comprising administering to a patient a therapeutically effective amount of a salt or a crystalline form as described herein.

In some embodiments, the present invention provides methods of treating a parasomnia comprising administering to a patient a therapeutically effective amount of a salt or a crystalline form as described herein.

In some embodiments, the present invention provides methods of treating a diabetic-related disorder comprising administering to a patient a therapeutically effective amount of a salt or a crystalline form as described herein.

In some embodiments, the present invention provides methods of treating progressive multifocal leukoencephalopathy comprising administering to a patient a therapeutically effective amount of a salt or a crystalline form as described herein.

In some embodiments, the present invention provides methods of treating hypertension comprising administering to a patient a therapeutically effective amount of a salt or a crystalline form as described herein.

In some embodiments, the present invention provides methods of treating pain comprising administering to a patient a therapeutically effective amount of a salt or a crystalline form as described herein.

In some embodiments, the present invention provides use of a compound or a salt or a crystalline form of the invention for use in therapy.

In some embodiments, the present invention provides use of a compound or a salt or a crystalline form of the invention for use in the preparation of a medicament for use in therapy.

DETAILED DESCRIPTION

The present invention is directed to processes and intermediates for the preparation of substituted phenyl-pyrazoles that are useful as 5-HT$_{2A}$ serotonin receptor modulators for the treatment of disorders associated with 5-HT$_{2A}$ serotonin receptor expression and/or activity such as, for example, central nervous system disorders (e.g., dementia, agitation or symptoms thereof, behavioral disorders, psychoses, organic or NOS psychosis, drug induced psychosis, excitative psychosis, Gilles de la Tourette's syndrome, manic disorder, psychotic disorder, schizophrenia, acute schizophrenia, chronic schizophrenia, NOS schizophrenia and related disorders, and the like), cardiovascular disorders (e.g., coronary artery disease, myocardial infarction, transient ischemic attack, angina, stroke, atrial fibrillation, platelet aggregation, blood clot formation, and the like), sleep disorders, asthma or symptoms thereof, diabetic-related disorders and the like.

Example processes and intermediates of the present invention are provided below in Scheme I, Scheme II and Scheme III, wherein each constituent member of the compounds depicted are defined herein.

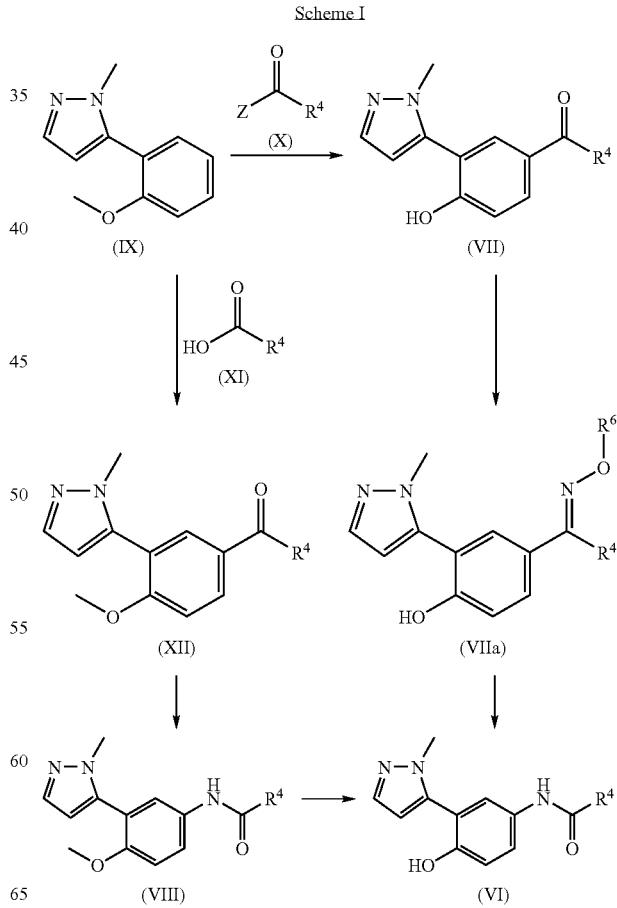

Scheme II

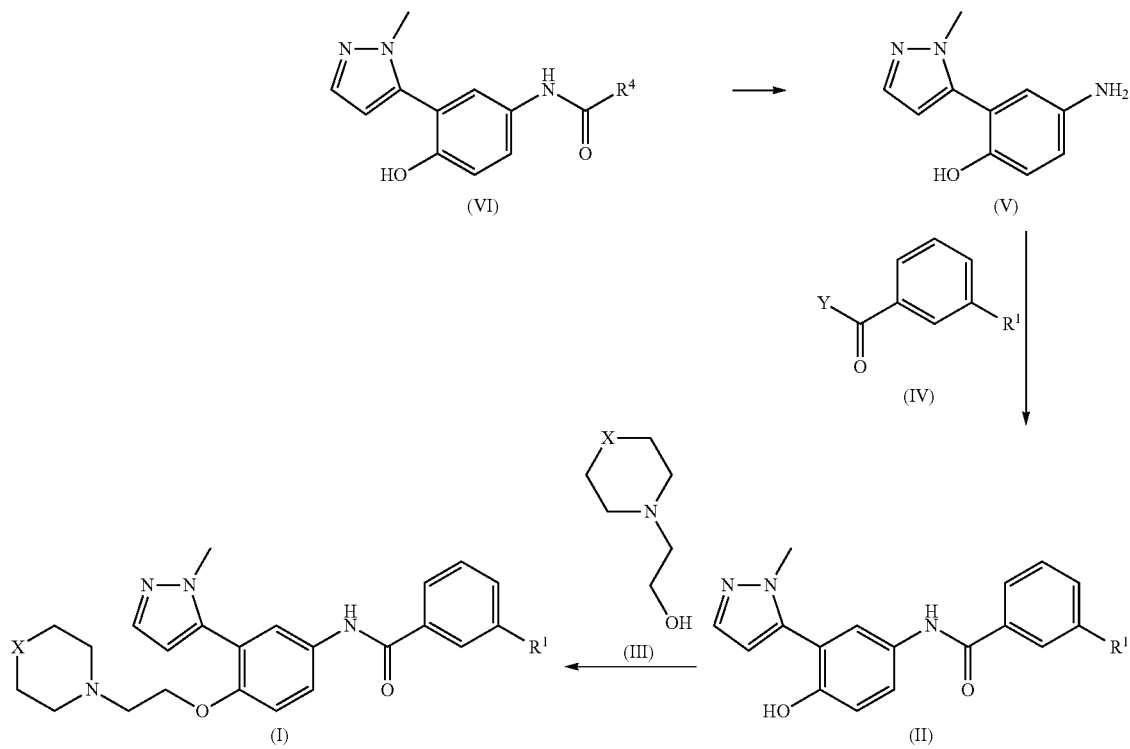

Scheme III

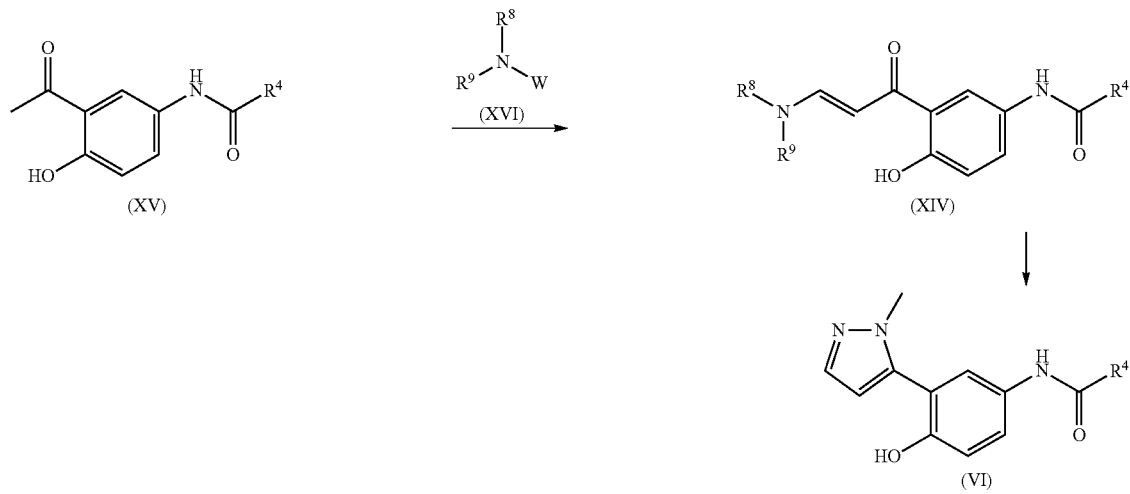

One aspect of the present invention pertains to processes, such as those exemplified by Scheme I, Scheme II and Scheme III (supra), that involve compounds of Formulae (I), (II), (III), (IV), (V), (VI), (VIIa), (VIII), (IX), (X), (XI), (XII), (XIV), (XV) and (XVI) or salt forms thereof, wherein:

$R^1$ is $C_1$-$C_8$ alkyl, halo, $C_1$-$C_8$ haloalkyl or $C_1$-$C_8$ alkoxy;

X is O, S, $NR^2$ or $CHR^2$;

$R^2$ is H, $C_1$-$C_8$ alkyl, $C_1$-$C_8$ acyl, $C_1$-$C_8$ alkenyl, $C_1$-$C_8$ alkynyl, $C_3$-$C_7$ cycloalkyl, $C_1$-$C_8$ haloalkyl, arylalkyl, aryl, heteroaryl or heteroarylalkyl each optionally substituted with $C_1$-$C_8$ alkyl, halo, $C_1$-$C_8$ haloalkyl or $C_1$-$C_8$ alkoxy;

Y is halo, OH or $OC(O)R^3$;

$R^3$ is $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, arylalkyl, aryl, heteroaryl or heteroarylalkyl each optionally substituted with $C_1$-$C_8$ alkyl, halo, $C_1$-$C_8$ haloalkyl or $C_1$-$C_8$ alkoxy; $C_1$-$C_8$ alkyl, $C_1$-$C_8$ alkenyl, $C_1$-$C_8$ alkynyl, $C_3$-$C_7$ cycloalkyl, arylalkyl, aryl, heteroaryl or heteroarylalkyl each optionally substituted with $C_1$-$C_8$ alkyl;

Z is halo or $OC(O)R^5$;

$R^5$ is $C_1$-$C_8$ alkyl, $C_1$-$C_8$ acyl, $C_1$-$C_8$ alkenyl, $C_1$-$C_8$ alkynyl, $C_3$-$C_7$ cycloalkyl, arylalkyl, aryl, heteroaryl or heteroarylalkyl each optionally substituted with $C_1$-$C_8$ alkyl;

$R^6$ is H, $C_1$-$C_8$ alkyl, $C_1$-$C_8$ alkenyl, $C_1$-$C_s$ alkynyl, or $SO_2R^7$;

$R^7$ is OH, $C_1$-$C_8$ alkyl, $C_1$-$C_8$ alkenyl, $C_1$-$C_8$ alkynyl or aryl optionally substituted with $C_1$-$C_8$ alkyl $R^8$ and $R^9$ are each independently $C_1$-$C_8$ alkyl or arylalkyl; or $R^8$ and $R^9$ together with the nitrogen atom to which they are both bonded form a heterocyclyl or a heterobicyclyl group;

W is formyl or —CH(OR$^{10}$)(OR$^{11}$); and $R^{10}$ and $R^{11}$ are each independently $C_1$-$C_8$ alkyl.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables ($R^1$, $R^2$, $R^3$, $R^4$, $R^5$, $R^6$, $R^7$, $R^8$, $R^9$, $R^{10}$, $R^{11}$, $R^a$, $R^b$, W, X, Y and Z) contained within the generic chemical formulae described herein [(I), (II), (III), (IV), (V), (VI), (VIIa), (VIII), (IX), (X), (XI), (XII), (XIV), (XV) and (XVI)] are specifically embraced by the present invention just as if they were explicitly disclosed, to the extent that such combinations embrace compounds that result in stable compounds (i.e., compounds that can be isolated, characterized and tested for biological activity).

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents and the like.

In some embodiments, $R^1$ is $C_1$-$C_8$ alkyl, halo, $C_1$-$C_8$ haloalkyl or $C_1$-$C_8$ alkoxy.

In some embodiments, $R^1$ is $C_1$-$C_8$ alkoxy.

In some embodiments, $R^1$ is methoxy.

In some embodiments, $R^1$ is halo.

In some embodiments, $R^1$ is fluoro.

In some embodiments, X is O, S, NR$^2$ or CHR$^2$.

In some embodiments, X is O

In some embodiments, X is NR$^2$ and $R^2$ is H, $C_1$-$C_8$ alkyl, $C_1$-$C_8$ acyl, $C_1$-$C_8$ alkenyl, $C_1$-$C_8$ alkynyl, $C_3$-$C_7$ cycloalkyl, $C_1$-$C_8$ haloalkyl, arylalkyl, aryl, heteroaryl or heteroarylalkyl each optionally substituted with $C_1$-$C_8$ alkyl, halo, $C_1$-$C_8$ haloalkyl or $C_1$-$C_8$ alkoxy.

In some embodiments, X is NR$^2$ and $R^2$ is $C_1$-$C_8$ acyl.

In some embodiments, X is NC(O)CH$_3$.

In some embodiments, $R^1$ is methoxy and X is O.

In some embodiments, $R^1$ is fluoro and $R^2$ is $C_1$-$C_8$ acyl.

In some embodiments, $R^1$ is fluoro and X is NC(O)CH$_3$.

In some embodiments, Y is halo, OH or OC(O)R$^3$.

In some embodiments, Y is halo and $R^1$ is methoxy.

In some embodiments, Y is halo and $R^1$ is fluoro.

In some embodiments, Y is chloro and $R^1$ is methoxy.

In some embodiments, Y is chloro and $R^1$ is fluoro.

In some embodiments, Y is OC(O)R$^3$ and $R^3$ is $C_1$-$C_8$ alkyl, $C_1$-$C_8$ alkenyl, $C_1$-$C_8$ alkynyl, $C_3$-$C_7$ cycloalkyl, $C_1$-$C_3$ haloalkyl, arylalkyl, aryl, heteroaryl or heteroarylalkyl each optionally substituted with $C_1$-$C_8$ alkyl, halo, $C_1$-$C_8$ haloalkyl or $C_1$-$C_8$ alkoxy.

In some embodiments, Y is OC(O)R$^3$ and $R^3$ is 3-methoxyphenyl.

In some embodiments, Y is OC(O)R$^3$ and $R^3$ is 3-fluorophenyl.

In some embodiments, Y is OC(O)R$^3$, $R^3$ is 3-methoxyphenyl and $R^1$ is methoxy.

In some embodiments, Y is OC(O)R$^3$, $R^3$ is 3-fluorophenyl and $R^1$ is fluoro.

In some embodiments, $R^4$ is $C_1$-$C_8$ alkyl, $C_1$-$C_8$ alkenyl, $C_1$-$C_8$ alkynyl, $C_3$-$C_7$ cycloalkyl, arylalkyl, aryl, heteroaryl or heteroarylalkyl each optionally substituted with $C_1$-$C_8$ alkyl.

In some embodiments, $R^4$ is $C_1$-$C_8$ alkyl.

In some embodiments, $R^4$ is methyl.

In some embodiments, Z is halo or OC(O)R$^5$.

In some embodiments, Z is halo.

In some embodiments, Z is halo and $R^4$ is $C_1$-$C_8$ alkyl.

In some embodiments, Z is halo and $R^4$ is methyl.

In some embodiments, Z is chloro and $R^4$ is $C_1$-$C_8$ alkyl.

In some embodiments, Z is chloro and $R^4$ is methyl.

In some embodiments, Z is OC(O)R$^5$ and $R^5$ is $C_1$-$C_8$ alkyl, $C_1$-$C_8$ acyl, $C_1$-$C_8$ alkenyl, $C_1$-$C_8$ alkynyl, $C_3$-$C_7$ cycloalkyl, arylalkyl, aryl, heteroaryl or heteroarylalkyl each optionally substituted with $C_1$-$C_8$ alkyl.

In some embodiments, Z is OC(O)R$^5$ and $R^4$ and $R^5$ are each $C_1$-$C_8$ alkyl.

In some embodiments, Z is OC(O)R$^5$ and $R^4$ and $R^5$ are each methyl.

In some embodiments:

$R^1$ is methoxy;

X is O;

Y is chloro;

$R^4$ is methyl; and

Z is chloro.

In some embodiments:

$R^1$ is fluoro;

X is NC(O)CH$_3$;

Y is chloro;

$R^4$ is methyl; and

Z is chloro.

In some embodiments, $R^8$ and $R^9$ are each independently $C_1$-$C_8$ alkyl or arylalkyl.

In some embodiments, $R^8$ and $R^9$ together with the nitrogen atom to which they are both bonded form a heterocyclyl or a heterobicyclyl group.

In some embodiments, $R^8$ and $R^9$ are each independently $C_1$-$C_8$ alkyl.

In some embodiments, $R^8$ and $R^9$ are both methyl.

In some embodiments, $R^8$ and $R^9$ are both ethyl.

In some embodiments, W is formyl.

In some embodiments, W is —CH(OR$^{10}$)(OR$^{11}$).

In some embodiments, W is —CH(OR$^{10}$)(OR$^{11}$) and $R^{10}$ and $R^{11}$ are each independently $C_1$-$C_8$ alkyl.

In some embodiments, W is —CH(OR$^{10}$)(OR$^{11}$) and $R^{10}$ and $R^{11}$ are both methyl.

In some embodiments, W is —CH(OR$^{10}$)(OR$^{11}$) and $R^{10}$ and $R^{11}$ are both ethyl.

In some embodiments:

$R^1$ is methoxy;

X is O;

Y is chloro;

$R^4$ is methyl;

$R^8$ is methyl;

$R^9$ is methyl;

W is —C(OR$^{10}$)(OR$^{11}$);

$R^{10}$ is methyl; and $R^{11}$ is methyl.

In some embodiments:
R[11] is fluoro;
X is NC(O)CH$_3$;
Y is chloro;
R[4] is methyl;
R[8] is methyl;
R[9] is methyl;
W is —C(OR[10])(OR[11]);
R[10] is methyl; and
R[11] is methyl.

Ether-Forming Step

The present invention provides, inter alia, processes for preparing compounds of Formula (I):

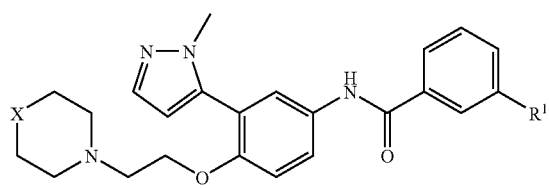

(I)

or a salt form thereof, comprising reacting a compound of Formula (II):

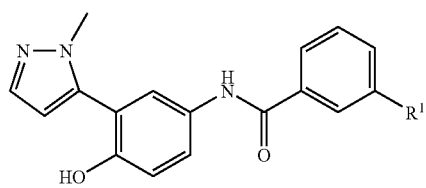

(II)

with a compound of Formula (III):

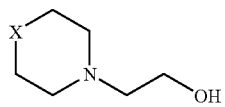

(III)

in the presence of a trisubstituted phosphine and a compound having the Formula (A):

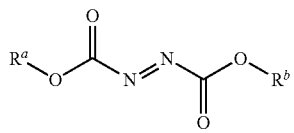

(A)

wherein, R$^a$ and R$^b$ are each, independently, C$_1$-C$_{10}$ alkyl or C$_3$-C$_7$ cycloalkyl to form a compound of Formula (I).

The trisubstituted phosphine can be any suitable tertiary phosphine such as a phosphine having the formula P(R)$_3$, where each R is, independently, C$_1$-C$_8$ alkyl, aryl, cycloalkyl, heteroaryl, heterocyclyl, arylalkyl, cycloalkylalkyl, heteroarylalkyl, or heterocyclicalkyl, each of which can be substituted by one or more halo, C$_3$-C$_4$ alkyl, C$_1$-C$_8$ haloalkyl, C$_1$-C$_4$ alkoxy, or C$_1$-C$_4$ haloalkoxy.

In some embodiments, the trisubstituted phosphine is a triarylphosphine.

In some embodiments, the trisubstituted phosphine is triphenylphosphine.

A suitable compound of Formula (A) can be readily selected by one skilled in the art. In some embodiments, R$^a$ and R$^b$ are each, independently, C$_1$-C$_{10}$ alkyl. In further embodiments, R$^a$ and R$^b$ are each, independently, C$_1$-C$_4$ alkyl. In yet further embodiments, R$^a$ and R$^b$ are both prop-2-yl.

In some embodiments, the compound of Formula (III) is added to a mixture containing the compound of Formula (II), the compound of Formula (A), and the trisubstituted phosphine.

In some embodiments, the compound of Formula (A) is added to a mixture containing the compound of Formula (II), the compound of Formula (III), and the trisubstituted phosphine.

In some embodiments, additional portions of phosphine and/or additional portions of the compound of Formula (A) and/or additional portions of the compound of Formula (III) can be added after the initial reacting.

In some embodiments, the total amount of phosphine is added in two or more portions.

In some embodiments, the total amount of compound of Formula (A) is added in two or more portions.

In some embodiments, the total amount of compound of Formula (III) is added in two or more portions.

The reacting of a compound of Formula (II) with a compound of Formula (III) can be carried out at any suitable temperature.

In some embodiments, the reacting is carried out at a temperature of about −50° C. to about 75° C.

In some embodiments, the reacting is carried out at a temperature of about −25° C. to about 50° C.

In some embodiments, the reacting is carried out at a temperature of about 0° C. to about 25° C.

The reacting of a compound of Formula (II) with a compound of Formula (III) can also be optionally carried out in a solvent. Suitable solvents can be readily selected by one skilled in the art. Example solvents include polar to moderately polar solvents or high boiling solvents such as N,N-dimethylformamide (DMF), N,N-dimethylacetamide, toluene, acetonitrile, propionitrile, tetrahydrofuran, N-methylpyrrolidinone, or tertiary amines including cyclic amines.

In some embodiments, the solvent is N-methylmorpholine.
In some embodiments, the solvent is an ether.
In some embodiments, the ether is a cyclic ether.
In some embodiments, the ether is tetrahydrofuran.

The reacting of a compound of Formula (II) with a compound of Formula (III) can be carried out where the molar ratio of compound of Formula (A) to compound of Formula (II) is about 4:1 to about 1:1, about 1.8:1 to about 1.2:1; or about 1.6:1 to about 1.4:1.

In some embodiments, the molar ratio of compound of Formula (A) to compound of Formula (II) is about 4:1 to about 1:1; about 1.8:1 to about 1.1:1; about 1.6:1 to about 1.2:1.

In some embodiments, the molar ratio of trisubstituted phosphine to compound of Formula (II) is about 4:1 to about 1:1, 1.8:1 to about 1.2:1, or about 1.6:1 to about 1.4:1.

In some embodiments, the molar ratio of trisubstituted phosphine to compound of Formula (II) is about 4:1 to about 1:1; 1.8:1 to about 1.1:1; or about 1.6:1 to about 1.4:1.

In further embodiments, the molar ratio of compound of Formula (A) to trisubstituted phosphine is about 1:1.

In yet further embodiments, the molar ratio of compound of Formula (II) to compound of Formula (III) is about 2.5:1 to about 0.5:1 or about 2:1 to about 1:1.

In yet further embodiments, the molar ratio of compound of Formula (III) to compound of Formula (II) is about 2.5:1 to about 0.5:1 or about 2:1 to about 1:1.

Amide-Forming Step

The present invention further provides processes for preparing compounds of Formula (II) comprising reacting a compound of Formula (IV):

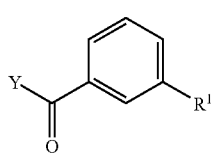

with a compound of Formula (V):

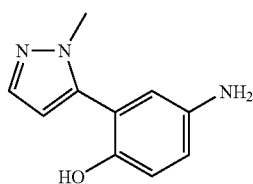

or a salt thereof to form a compound of Formula (II).

In some embodiments, Y is halo or $OC(O)R^3$ and $R^3$ is $C_1$-$C_8$ alkyl, $C_1$-$C_3$ alkenyl, $C_1$-$C_8$ alkynyl, $C_3$-$C_7$ cycloalkyl, $C_1$-$C_8$ haloalkyl, arylalkyl, aryl, heteroaryl or heteroarylalkyl each optionally substituted with $C_1$-$C_8$ alkyl, halo, $C_1$-$C_8$ haloalkyl or $C_1$-$C_8$ alkoxy.

In some embodiments, the reacting of a compound of Formula (IV) with a compound of Formula (V) can be optionally carried out in the presence of any suitable base, readily selected by one skilled in the art.

In some embodiments, the base is an inorganic base. Examples of inorganic bases include ammonia and carbonates, hydroxides and hydrogen carbonates of metals such as sodium, potassium, magnesium, calcium, cesium and the like.

In some embodiments, the base is an organic base. Examples of organic bases include aliphatic and aromatic amines such as triethylamine, N-ethyldiisopropylamine, dibenzylamine or pyridine.

In some embodiments, the base is a mixture of pyridine and N,N-dimethylaminopyridine.

In some embodiments, the base is N-methylmorpholine

In some embodiments, the base is sodium bicarbonate.

In some embodiments, the base is pyridine.

In some embodiments, the Y is OH and the reacting of a compound of Formula (IV) with a compound of Formula (V) can be optionally carried out in the presence of any suitable coupling agent, readily selected by one skilled in the art. Examples of coupling reagents include, but are not limited to, HATU, HOAt, HODhbt, HAPyU, TAPipU, HBTU, TBTU, TPTU, TSTU, TNTU, TOTU, BOP, PyBOP, BroP, PyBroP, BOI, MSNT, TDO, DCC, EDCI, CDI, HOBt, HOSu, NEPIS, BBC, BDMP, BOW, AOP, BDP, PyAOP, TDBTU, BOP-Cl, CIP, DEPBT, Dpp-Cl, EEDQ, FDPP, HOTT, TOTT, PyCloP, and the like.

The reacting of a compound of Formula (IV) with a compound of Formula (V) can be optionally carried out in the presence of any suitable solvent readily selected by one skilled in the art. Example solvents include polar to moderately polar solvents or high boiling solvents such as N,N-dimethylformamide, N,N-dimethylacetamide, toluene, acetonitrile, propionitrile, tetrahydrofuran, N-methylpyrrolidinone, or tertiary amines including cyclic amines.

In some embodiments, the solvent is a polar, aprotic solvent. Example solvents include N,N-dimethylformamide, N,N-dimethylacetamide, N-methylpyrrolidinone and the like.

In some embodiments, the solvent is an amide.

In some embodiments, the solvent is N,N-dimethylacetamide.

In some embodiments, the solvent is an alcohol such as ethanol, n-propanol, isopropanol, n-butanol and the like.

In some embodiments, the solvent is isopropanol.

In some embodiments, the reacting of a compound of Formula (IV) with a compound of Formula (V) can be carried out at any suitable temperature.

In some embodiments, the reacting is carried out at a temperature of about −60° C. to about 75° C.

In some embodiments, the reacting is carried out at a temperature of about −35° C. to about 50° C.

In some embodiments, the reacting is carried out at a temperature of about −10° C. to about 25° C.

Amide Cleavage Step

The present invention further provides processes for preparing a compound of Formula (V) comprising reacting a compound of Formula (VI):

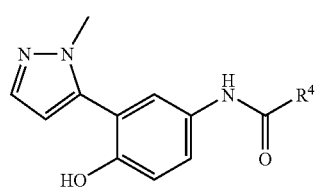

with a cleaving reagent to form a compound of Formula (V) or a salt thereof.

In some embodiments, the compound of Formula (V) may be prepared by reacting a compound of Formula (VI) with any of the numerous amide-cleaving agents known in the art. Examples of cleaving agents include but are not limited to HCl, hydrazine, $H_2$/palladium, hydrogen peroxide, sodium hydroxide, triethyloxonium tetrafluoroborate, acylases, sodium, sodium methoxide, sodium borohydride, potassium carbonate, ammonia, iodine, copper acetate, HF and DIBAL. The chemistry of amide deprotections can be found, for example, in Greene and Wuts, *Protective Groups in Organic Synthesis*, 3$^{rd}$ Ed., Wiley & Sons, 1999, which is incorporated herein by reference in its entirety.

In some embodiments, the cleaving reagent is an acid. Examples of acids include hydrochloric acid, hydrobromic acid, methanesulfonic acid, trifluoromethanesulfonic acid, sulfuric acid and the like.

In some embodiments, the cleaving reagent is sulfuric acid.

The reacting of a compound of Formula (VI) with a cleaving reagent can be optionally carried out in the presence of any suitable solvent, readily selected by one skilled in the art.

In some embodiments, the solvent is an alcohol such as methanol, ethanol, n-propanol, isopropanol, n-butanol and the like.

In some embodiments, the solvent is methanol.

The reacting of a compound of Formula (VI) with a cleaving reagent can be carried out at any suitable temperature, readily selected by one skilled in the art.

In some embodiments, the reacting is carried out at a temperature of about 25° C. to about 90° C.

In some embodiments, the reacting is carried out at a temperature of about 40° C. to about 80° C.

In some embodiments, the reacting is carried out at a temperature of about 60° C. to about 75° C.

In some embodiments, the reacting is carried out at a temperature of about 25° C. to about 65° C.

In some embodiments, the reacting is carried out at a temperature of about 30° C. to about 60° C.

In some embodiments, the reacting is carried out at a temperature of about 40° C. to about 55° C.

Rearrangement Step

The present invention further provides processes for preparing compounds of Formula (VI) comprising reacting a compound of Formula (VII):

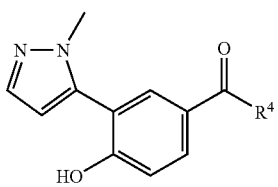

(VII)

with an amine in the presence of an acid to form a compound of Formula (VI).

In some embodiments, the acid is added in two or more portions wherein the second portion is added after the formation of a compound of the Formula (VIIa):

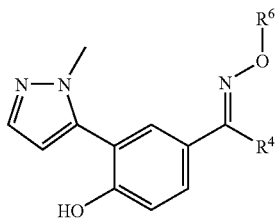

(VIIa)

formed by the reacting of a compound of Formula (VII) with an amine in the presence of an acid.

In some embodiments, $R^4$ is $C_1$-$C_8$ alkyl, $C_1$-$C_8$ alkenyl, $C_1$-$C_8$ alkynyl, $C_3$-$C_7$ cycloalkyl, arylalkyl, aryl, heteroaryl or heteroarylalkyl each optionally substituted with $C_1$-$C_8$ alkyl.

In some embodiments, $R^4$ is $C_1$-$C_8$ alkyl.

In some embodiments, $R^4$ is methyl.

In some embodiments, $R^6$ is H, $C_1$-$C_8$ alkyl, $C_1$-$C_8$ alkenyl, $C_1$-$C_8$ alkynyl, or $SO_2R^7$ and $R^7$ is OH, $C_1$-$C_8$ alkyl, $C_1$-$C_8$ alkenyl, $C_1$-$C_8$ alkynyl or aryl optionally substituted with $C_1$-$C_8$ alkyl.

In some embodiments, $R^6$ is H.

By way of example, the molecular ion (m/z 232.3) of the compound of Formula (VIIa) wherein $R^4$ is methyl and $R^6$ is H was observed by mass spectrometry in the reacting of the compound of Formula (VII) with hydroxylamine in the presence of sulfuric acid. In some embodiments, the amine is hydroxylamine.

In some embodiments, the amine is a salt of hydroxylamine. Examples of hydroxylamine salts include but are not limited to HCl, phosphate, oxalate, nitrate, EDTA and sulfate.

In some embodiments, the amine is hydroxylamine hydrochloride. The acid can be any suitable acid, readily selected by one skilled in the art.

In some embodiments, the acid is sulfuric acid.

The reacting of a compound of Formula (VII) with an amine can be optionally carried out in the presence of any suitable solvent, readily selected by one skilled in the art.

In some embodiments, the solvent is a carboxylic acid, such as, formic acid, acetic acid, propionic acid, butyric acid, isobutyric acid and the like.

In some embodiments, the solvent is acetic acid.

The reacting of a compound of Formula (VI) with a cleaving reagent can be carried out at any suitable temperature, readily selected by one skilled in the art.

In some embodiments, the reacting is carried out at a temperature of about 25° C. to about 105° C.

In some embodiments, the reacting is carried out at a temperature of about 50° C. to about 95° C.

In some embodiments, the reacting is carried out at a temperature of about 75° C. to about 85° C.

Acylation Step

The present invention further provides processes for preparing compounds of Formula (VII) comprising reacting a compound of Formula (IX):

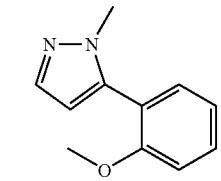

(IX)

with a compound of the Formula (X):

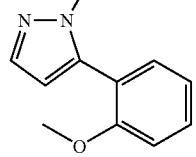

(X)

in the presence of a Lewis acid to form a compound of Formula (VII).

The Lewis acid can be any suitable Lewis acid, readily selected by one skilled in the art. Examples of Lewis acids include $AlCl_3$, $FeCl_3$, $ZnCl_2$, $AlBr_3$; $ZnBr_2$, $TiCl_4$, $SnCl_4$ and the like.

In some embodiments, the Lewis acid is $AlCl_3$.

The reacting of a compound of Formula (IX) with a compound of Formula (X) can be optionally carried out in the presence of any suitable solvent, readily selected by one skilled in the art. Examples of suitable solvents include carbon disulfide; ethers such as diethyl ether, MTBE and THF; haloalkanes such as dichloromethane, 1,2-dichloroethane and chloroform; nitroalkanes such as nitromethane and nitroethane; nitriles such as acetonitrile and propionitrile; and aromatic solvents such as benzene, toluene, pyridine, chlorobenzene, nitrobenzene and the like.

In some embodiments, the solvent is a high-boiling aromatic solvent.

In some embodiments, the solvent is 1,2-dichlorobenzene.

The reacting of a compound of Formula (IX) with a with a compound of the Formula (X) can be carried out at any suitable temperature, readily selected by one skilled in the art.

In some embodiments, the reacting is carried out at a temperature of about 25° C. to about 175° C.

In some embodiments, the reacting is carried out at a temperature of about 50° C. to about 130° C.

In some embodiments, the reacting is carried out at a temperature of about 75° C. to about 85° C.

Demethylation Step

The present invention further provides processes for preparing compounds of Formula (VI) comprising reacting a compound of Formula (VIII):

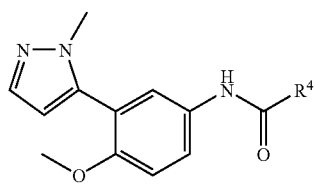

(VIII)

with a demethylating agent to form a compound of Formula (VI).

The demethylating agent can be any suitable reagent, readily selected by one skilled in the art. Examples of demethylating agents include trimethylsilyliodide; Lewis acids such as $BCl_3$, $BBr_3$, $BI_3$, $AlCl_3$, $AlBr_3$, $TiCl_4$ and $SnCl_4$; HBr in acetic acid; thiolates such as sodium sulfide, $C_1$-$C_{18}$ alkyl thiolates, sodium thiocresolate, potassium thiophenoxide and sodium trimethylsilanethiolate; sodium benzyl selenide; alkali metals such as sodium/$NH_3$ and potassium/18-crown-6; lithium halides; strong bases such as NaRMDS and LDA; sodium cyanide in DMSO or 9-Br-BBN and the like.

In some embodiments, the demethylating agent is a $C_1$-$C_{18}$ alkyl thiolate.

In some embodiments, the demethylating agent is a sodium dodecyl thiolate.

The reacting of a compound of Formula (VIII) with a demethylating agent can be optionally carried out in the presence of any suitable solvent, readily selected by one skilled in the art. Examples of suitable solvents include acids such as acetic acid or propionic acid; ethers such as diethyl ether, MTBE and THF; haloalkanes such as dichloromethane, 1,2-dichloroethane and chloroform or amides such as N,N-dimethylformamide and N,N-dimethylacetamide and N-methylpyrrolidinone and the like.

In some embodiments, the solvent is an amide.

In some embodiments, the solvent is N,N-dimethylacetamide.

The reacting of a compound of Formula (VIII) with a demethylating agent can be carried out at any suitable temperature, readily selected by one skilled in the art.

In some embodiments, the reacting is carried out at a temperature of about 25° C. to about 165° C.

In some embodiments, the reacting is carried out at a temperature of about 75° C. to about 155° C.

In some embodiments, the reacting is carried out at a temperature of about 130° C. to about 145° C.

Acylation-Rearrangement Step

The present invention further provides processes for preparing compounds of Formula (VIII) comprising reacting a compound of Formula (IX):

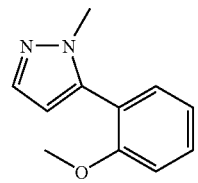

(IX)

with a compound of Formula (XI):

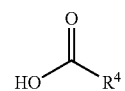

(XI)

and an amine to form a compound of Formula (VIII).

In some embodiments, the amine is present at the start of the reacting whereby the acylation and rearrangement steps are telescoped into a single process.

In some embodiments, the amine is added in situ after the formation of an intermediate of Formula (XII):

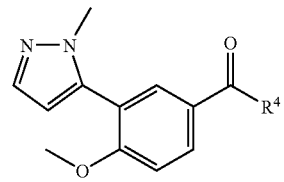

(XII)

formed by acylating the compound of Formula (IX) with a compound of Formula (XI).

In some embodiments, the amine is hydroxylamine.

In some embodiments, the amine is a salt of hydroxylamine. Examples of hydroxylamine salts include but are not limited to HCl, phosphate, oxalate, nitrate, EDTA and sulfate.

In some embodiments, the amine is hydroxylamine hydrochloride.

The reacting of a compound of Formula (IX) with a compound of Formula (XI) and an amine can be optionally carried out in the presence of any suitable solvent, readily selected by one skilled in the art.

In some embodiments, the solvent is phosphoric acid.

In some embodiments, the solvent is phosphorous pentoxide in methanesulfonic acid (Eaton's Reagent).

The reacting of a compound of Formula (IX) with a compound of Formula (XI) and an amine can be carried out at any suitable temperature, readily selected by one skilled in the art.

In some embodiments, the reacting is carried out at a temperature of about 20° C. to about 140° C.

In some embodiments, the reacting is carried out at a temperature of about 40° C. to about 120° C.

In some embodiments, the reacting is carried out at a temperature of about 60° C. to about 100° C.

Pyrazole Formation Step

The present invention further provides processes for preparing compounds of Formula (VI) comprising reacting a compound of Formula (XIV):

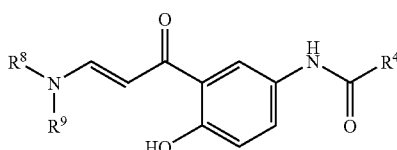

with methyl hydrazine in the presence of a catalyst to form said compound of Formula (VI).

The catalyst can be any suitable catalyst, readily selected by one skilled in the art. Examples of suitable catalysts include Lewis acids, Brønsted acids, organic acids, inorganic acids, organic bases, inorganic bases and montmorillonites.

In some embodiments, the catalyst is a Lewis acid. Examples of Lewis acids include $BF_3$, $BCl_3$, $BBr_3$, $BI_3$, $AlCl_3$, $FeCl_3$, $ZnCl_2$, $AlBr_3$, $ZnBr_2$, $TiCl_4$, $SnCl_4$ and the like.

In some embodiments, the Lewis acid is boron trifluoride diethyletherate.

In some embodiments, $R^8$ and $R^9$ are each independently $C_1$-$C_8$ alkyl or arylalkyl.

In some embodiments, $R^8$ and $R^9$ together with the nitrogen atom to which they are both bonded form a heterocyclyl or a heterobicyclyl group.

In some embodiments, $R^8$ and $R^9$ are each independently $C_1$-$C_8$ alkyl.

In some embodiments, $R^8$ and $R^9$ are both methyl.

The reacting of a compound of Formula (XIV) with methyl hydrazine can be optionally carried out in the presence of any suitable solvent, readily selected by one skilled in the art.

In some embodiments, the solvent is an alcohol such as methanol, ethanol, n-propanol, isopropanol, n-butanol and the like.

In some embodiments, the solvent is methanol.

The reacting of compound of Formula (XIV) with methyl hydrazine can be carried out at any suitable temperature.

In some embodiments, the reacting is carried out at a temperature of about −20° C. to about 30° C.

In some embodiments, the reacting is carried out at a temperature of about −10° C. to about 20° C.

In some embodiments, the reacting is carried out at a temperature of about 0° C. to about 10° C.

Enaminone Formation Step

The present invention further provides processes for preparing compounds of Formula (XIV) comprising reacting a compound of Formula (XV):

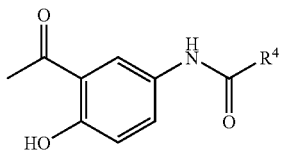

with a compound of Formula (XVI):

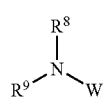

to form said compound of Formula (XIV).

In some embodiments, W is formyl.

In some embodiments, W is —CH(OR$^{10}$)(OR$^{11}$) and $R^{10}$ and $R^{11}$ are each independently $C_1$-$C_8$ alkyl;

In some embodiments, W is —CH(OR$^{10}$)(OR$^{11}$) and $R^{10}$ and $R^{11}$ are both methyl.

The reacting of a compound of Formula (XV) with a compound of Formula (XVI) can be optionally carried out in the presence of any suitable solvent, readily selected by one skilled in the art.

In some embodiments, the solvent is an alcohol such as methanol, ethanol, n-propanol, isopropanol, n-butanol and the like.

In some embodiments, the solvent is isopropanol.

The reacting of a compound of Formula (XV) with a compound of Formula (XVI) can be carried out at any suitable temperature.

In some embodiments, the reacting is carried out at a temperature of about 20° C. to about 90° C.

In some embodiments, the reacting is carried out at a temperature of about 30° C. to about 70° C.

In some embodiments, the reacting is carried out at a temperature of about 40° C. to about 50° C.

Salt Formation

The present invention further provides processes for preparing salts of compounds of Formula (I):

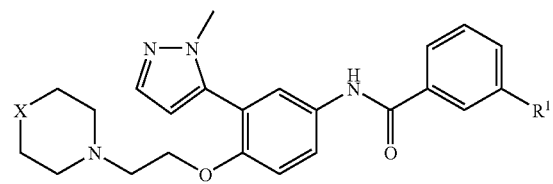

comprising reacting a compound of Formula (I) with a salt-forming acid to form a salt of a compound of Formula (I) provided that the salt-forming acid is not trifluoroacetic acid.

In some embodiments, $R^1$ is $C_1$-$C_8$ alkyl, halo, $C_1$-$C_8$ haloalkyl or $C_1$-$C_8$ alkoxy.

In some embodiments, $R^1$ is $C_1$-$C_8$ alkoxy.

In some embodiments, $R^1$ is methoxy.

In some embodiments, $R^1$ is halo.

In some embodiments, $R^1$ is fluoro.

In some embodiments, X is O, S, $NR^2$ or $CHR^2$.

In some embodiments, X is O

In some embodiments, X is $NR^2$ and $R^2$ is H, $C_1$-$C_8$ alkyl, $C_8$-$C_8$ acyl, $C_1$-$C_8$ alkenyl, $C_1$-$C_8$ alkynyl, $C_3$-$C_7$ cycloalkyl, $C_1$-$C_8$ haloalkyl, arylalkyl, aryl, heteroaryl or heteroarylalkyl each optionally substituted with $C_1$-$C_8$ alkyl, halo, $C_1$-$C_8$ haloalkyl or $C_1$-$C_8$ alkoxy.

In some embodiments, X is $NR^2$ and $R^2$ is $C_1$-$C_8$ acyl.

In some embodiments, X is $NC(O)CH_3$.

In some embodiments, $R^1$ is methoxy and X is O.

In some embodiments, $R^1$ is fluoro and $R^2$ is $C_1$-$C_8$ acyl.

In some embodiments, $R^1$ is fluoro and X is $NC(O)CH_3$.

In some embodiments, the salt-forming acid is hydrochloric acid.

In some embodiments, the salt-forming acid is oxalic acid.

The reacting of a compound of Formula (I) with a salt-forming acid to form a salt of a compound of Formula (I) can be optionally carried out in the presence of any suitable solvent, readily selected by one skilled in the art.

In some embodiments, the solvent is an alcohol such as methanol, ethanol, n-propanol, isopropanol, n-butanol and the like.

In some embodiments, the solvent is methanol.

In some embodiments, the solvent is isopropanol.

In some embodiments, the solvent is ethanol.

The reacting of a compound of Formula (I) with a salt-forming acid to form a salt of a compound of Formula (I) can be carried out at any suitable temperature, readily selected by one skilled in the art.

In some embodiments, the reacting is carried out at a temperature above the freezing point of the solvent to about the reflux temperature of the solvent.

In some embodiments, the reacting is carried out at a temperature of about −10° C. to about reflux temperature.

In some embodiments, the reacting is carried out at a temperature of about 10° C. to about 80° C.

In some embodiments, the reacting is carried out at a temperature of about 20° C. to about 80° C.

Pharmaceutically Acceptable Salts

Some embodiments of the present invention pertain to pharmaceutically acceptable salts of compounds of Formula (I):

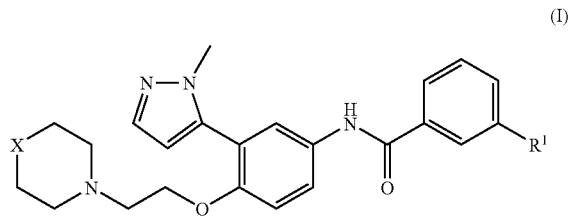

provided that the pharmaceutically acceptable salt is not a trifluoroacetate salt.

In some embodiments, $R^1$ is $C_1$-$C_8$ alkyl, halo, $C_1$-$C_8$ haloalkyl or $C_1$-$C_8$ alkoxy.

In some embodiments, $R^1$ is $C_1$-$C_8$ alkoxy.

In some embodiments, $R^1$ is methoxy.

In some embodiments, $R^1$ is halo.

In some embodiments, $R^1$ is fluoro.

In some embodiments, X is O, S, $NR^2$ or $CHR^2$.

In some embodiments, X is O

In some embodiments, X is $NR^2$ and $R^2$ is H, $C_1$-$C_8$ alkyl, $C_1$-$C_8$ acyl, $C_1$-$C_8$ alkenyl, $C_1$-$C_8$ alkynyl, $C_3$-$C_7$ cycloalkyl, $C_1$-$C_8$ haloalkyl, arylalkyl, aryl, heteroaryl or heteroarylalkyl each optionally substituted with $C_1$-$C_8$ alkyl, halo, $C_1$-$C_8$ haloalkyl or $C_1$-$C_8$ alkoxy.

In some embodiments, X is $NR^2$ and $R^2$ is $C_1$-$C_8$ acyl.

In some embodiments, X is $NC(O)CH_3$.

In some embodiments, $R^1$ is methoxy and X is O.

In some embodiments, W is fluoro and $R^2$ is $C_1$-$C_8$ acyl.

In some embodiments, $R^1$ is fluoro and X is $NC(O)CH_3$.

In some embodiments, the pharmaceutically acceptable salt has a purity of 80% or greater.

In some embodiments, the pharmaceutically acceptable salt has a purity of 90% or greater.

In some embodiments, the pharmaceutically acceptable salt has a purity of 95% or greater.

In some embodiments, the pharmaceutically acceptable salt has a purity of 99% or greater.

In some embodiments, the pharmaceutically acceptable salt has a purity of 99.5% or greater.

In some embodiments, the pharmaceutically acceptable salt comprises a pharmaceutically acceptable salt of a compound of Formula (I) and a compound of Formula (I) in a ratio of about 4:1 or greater.

In some embodiments, the pharmaceutically acceptable salt comprises a pharmaceutically acceptable salt of a compound of Formula (I) and a compound of Formula (I) in a ratio of about 9:1 or greater.

In some embodiments, the pharmaceutically acceptable salt comprises a pharmaceutically acceptable salt of a compound of Formula (I) and a compound of Formula (I) in a ratio of about 19:1 or greater.

In some embodiments, the pharmaceutically acceptable salt comprises a pharmaceutically acceptable salt of a compound of Formula (I) and a compound of Formula (I) in a ratio of about 99:1 or greater.

In some embodiments, the pharmaceutically acceptable salt is a hydrochloride salt.

In some embodiments, the pharmaceutically acceptable salt is an oxalate salt.

Intermediates

The present invention further provides intermediates that are useful in the preparation of compounds of Formula (I) and salts thereof.

Some embodiments pertain to compounds of Formula (II):

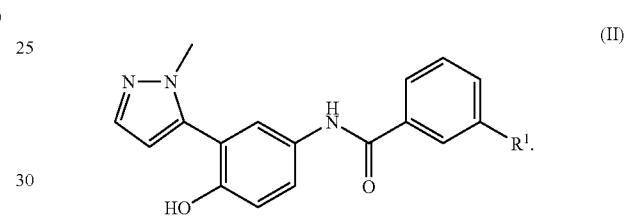

Some embodiments pertain to compounds of Formula (II) and salts thereof.

In some embodiments, $R^1$ is $C_1$-$C_8$ alkyl, halo, $C_1$-$C_8$ haloalkyl or $C_1$-$C_8$ alkoxy.

In some embodiments, $R^1$ is $C_1$-$C_8$ alkoxy.

In some embodiments, $R^1$ is methoxy.

In some embodiments, $R^1$ is halo.

In some embodiments, $R^1$ is fluoro.

Some embodiments pertain to a compound of Formula (V):

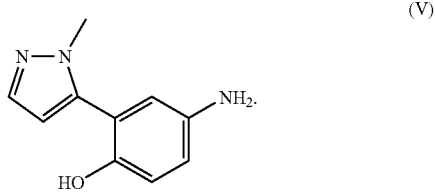

Some embodiments pertain to compounds of Formula (VII):

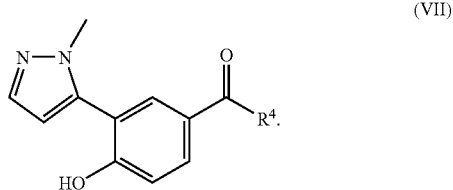

Some embodiments pertain to compounds of Formula (VII) and salts thereof.

In some embodiments, $R^4$ is $C_1$-$C_8$ alkyl, $C_1$-$C_8$ alkenyl, $C_1$-$C_8$ alkynyl, $C_3$-$C_7$ cycloalkyl, arylalkyl, aryl, heteroaryl or heteroarylalkyl each optionally substituted with $C_1$-$C_8$ alkyl.

minus about 0.2°. The physical properties of the crystalline forms of compound 7 and compound 9 of the invention are summarized in Table I below.

TABLE 1

|  | Compound 7 Form I | Compound 9 Form I |
|---|---|---|
| TGA | FIG. 1: negligible weight loss below 150° C. | FIG. 5: total weight loss of 0.7% observed up to ~240° C. |
| DSC | FIG. 2: 218° C. (melt) | FIG. 6: 240° C. (melt) |
| XRPD | FIG. 3: Peaks of ≧30% relative intensity at 5.2, 14.4, 15.3, 15.8, 17.3, 19.8, 20.1, 23.1, 25.6 and 27.1 °2θ | FIG. 7: Peaks of ≧2% relative intensity at 7.0, 12.5, 13.9, 18.6, 20.9, 23.2, 26.0 and 33.4 °2θ |
| DVS | FIG. 4: Non-hygroscopic; absorption of less than 0.4% at 95% relative humidity | FIG. 8: Absorption of about 11% at 95% relative humidity |
| Habit | Plates | Not Known |

In some embodiments, $R^4$ is $C_1$-$C_8$ alkyl.
In some embodiments, $R^4$ is methyl.
Some embodiments pertain to compounds of Formula (VIIa):

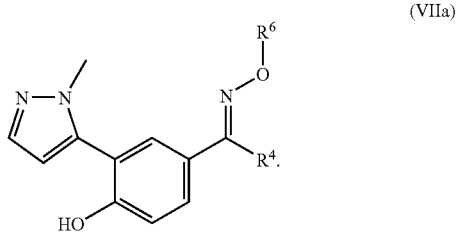

(VIIa)

In some embodiments, $R^4$ is $C_1$-$C_8$ alkyl, $C_1$-$C_8$ alkenyl, $C_1$-$C_8$ alkynyl, $C_3$-$C_7$ cycloalkyl, arylalkyl, aryl, heteroaryl or heteroarylalkyl each optionally substituted with $C_1$-$C_8$ alkyl.

In some embodiments, $R^4$ is $C_1$-$C_8$ alkyl.
In some embodiments, $R^4$ is methyl.
In some embodiments, $R^6$ is H, $C_1$-$C_8$ alkyl, $C_1$-$C_a$ alkenyl, $C_1$-$C_8$ alkynyl, or $SO_2R^7$ and $R^7$ is OH, $C_1$-$C_8$ alkyl, $C_1$-$C_8$ alkenyl, $C_1$-$C_8$ alkynyl or aryl optionally substituted with $C_1$-$C_8$ alkyl.
In some embodiments, $R^6$ is H.

Crystalline Forms

The crystalline form of 4-(2-(4-(3-methoxybenzamido)-2-(1-methyl-1H-pyrazol-5-yl)phenoxy)ethyl)morpholin-4-ium chloride (Compound 7), designated Form I, and the crystalline form of 4-acetyl-1-(2-(4-(3-fluorobenzamido)-2-(1-methyl-1H-pyrazol-5-yl)phenoxy)ethyl)piperazin-1-ium carboxyformate (Compound 9), designated Form I can be identified by their unique solid state signatures with respect to, for example, differential scanning calorimetry (DSC), X-ray powder diffraction (XRPD), and other solid state methods. Further characterization with respect to water or solvent content of the crystalline forms can be gauged by any of the following methods for example, thermogravimetric analysis (TGA), DSC and the like. For DSC, it is known that the temperatures observed will depend upon the rate of temperature change as well as sample preparation technique and the particular instrument employed. Thus, the values reported herein relating to DSC thermograms can vary by plus or minus about 4° C. For XRPD, the relative intensities of the peaks can vary, depending upon the sample preparation technique, the sample mounting procedure and the particular instrument employed. Moreover, instrument variation and other factors can often affect the 2-theta values. Therefore, the peak assignments of diffraction patterns can vary by plus or The negligible weight loss observed in the TGA data suggests that both Compound 7 Form I and Compound 9 Form I are anhydrous, non-solvated crystal forms. The individual DSC traces further reveal a melting/decomposition endotherm at about 218° C. for Compound 7 Form I and a melting/decomposition endotherm at about 240° C. for Compound 9 Form I.

DVS data for Compound 7 Form I reveals that it is non-hygroscopic, with absorption of less than 0.4% at 95% relative humidity. In contrast, the DVS data in connection with Compound 9 Form I reveals that it absorbs about 11% at 95% relative humidity.

X-ray powder diffraction peaks for Compound 7 Form I and Compound 9 Form I are shown in Tables 2 and 3 below.

TABLE 2

| Compound 7 Form I (degrees 2θ) |
|---|
| 5.2 |
| 9.8 |
| 12.1 |
| 13.0 |
| 13.5 |
| 14.4 |
| 15.1 |
| 15.3 |
| 15.8 |
| 16.1 |
| 16.5 |
| 17.3 |
| 17.9 |
| 19.0 |
| 19.5 |
| 19.8 |
| 20.1 |
| 20.4 |
| 21.0 |
| 21.4 |
| 21.6 |
| 22.7 |
| 23.1 |
| 23.7 |
| 24.2 |
| 24.6 |
| 25.2 |
| 25.6 |
| 26.0 |
| 27.1 |
| 27.5 |
| 28.0 |
| 28.6 |
| 29.5 |
| 30.0 |
| 30.4 |
| 31.2 |
| 31.5 |

TABLE 2-continued

Compound 7 Form I (degrees 2θ)

32.3
32.7
33.8
34.1
34.7
36.0
36.6
37.1
37.5
37.8
39.0
39.4

TABLE 3

Compound 9 Form I (degrees 2θ)

5.1
7.0
9.5
11.0
12.5
13.9
14.5
15.5
15.9
16.7
17.8
18.6
19.1
19.6
20.1
20.3
20.9
22.3
23.2
24.4
24.9
26.0
26.6
27.2
27.9
29.0
29.6
30.6
31.1
31.5
32.0
32.8
33.4
34.6
35.3
37.5
38.5

Compound 7 Form I

Figure 3:
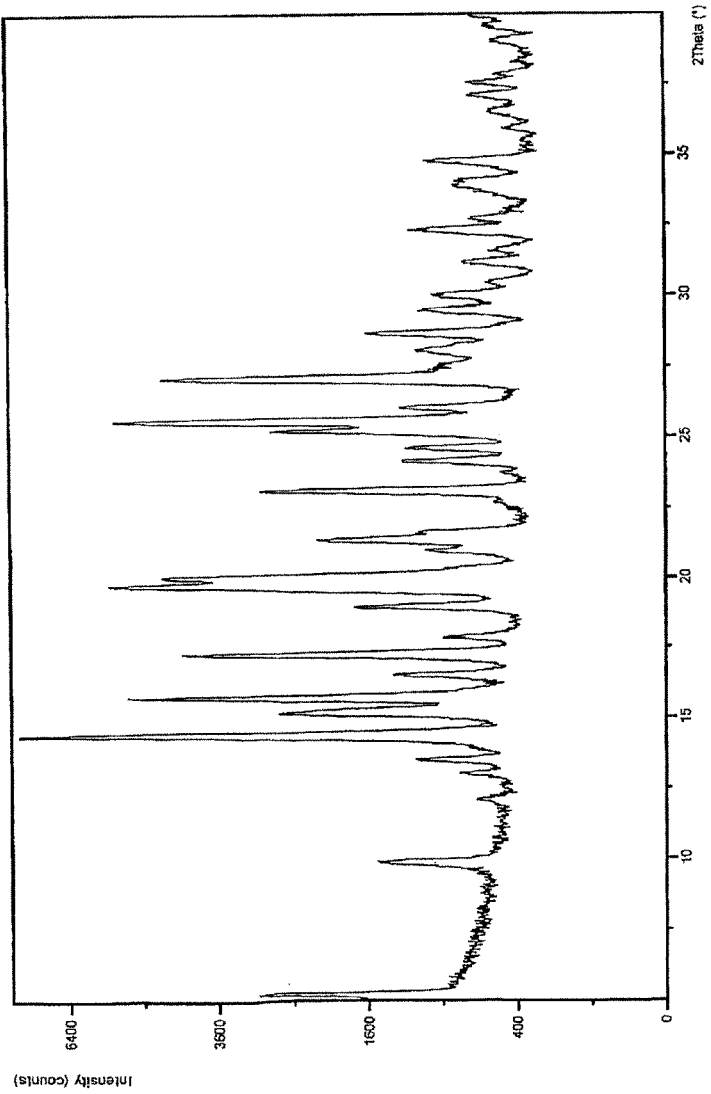
FIG. 3 depicts a powder X-ray diffraction pattern (XRPD) for a sample containing crystalline Form I of Compound 7 (PANalytical X'Pert Plus Powder X-Ray Diffractometer; 5.0°-40.0° 2θ).

One aspect of the present invention is directed to a crystalline form of 4-(2-(4-(3-methoxybenzamido)-2-(1-methyl-1H-pyrazol-5-yl)phenoxy)ethyl)morpholin-4-ium chloride (Form I) having an X-ray powder diffraction pattern comprising a peak, in terms of 2θ, at about 14.4°. In some embodiments, the crystalline form has an X-ray powder diffraction pattern comprising a peak, in terms of 2θ, at about 5.2°. In some embodiments, the crystalline form has an X-ray powder diffraction pattern comprising peaks, in terms of 2θ, at about 14.4° and about 25.6°. In some embodiments, the crystalline form has an X-ray powder diffraction pattern comprising peaks, in terms of 2θ, at about 5.2° and about 25.6°. In some embodiments, the crystalline form has am X-ray powder diffraction pattern comprising peaks, in terms of 2θ, at about 14.4°, about 5.2°, and about 25.6°. In some embodiments, the crystalline form has an X-ray powder diffraction pattern comprising peaks, in terms of 2θ, at about 14.4°, about 5.2°, about 25.6°, about 17.3°, about 27.1°, about 15.8°, and about 20.1°. In further embodiments, the crystalline form has an X-ray powder diffraction pattern comprising peaks, in terms of 2θ, at about 14.4°, about 5.2°, about 25.6°, about 17.3°, about 27.1°, about 15.8°, about 20.1°, about 19.8°, about 23.1° and about 15.3°. In yet further embodiments, the crystalline form has an X-ray powder diffraction pattern substantially as shown in FIG. 3, wherein by "substantially" is meant that the reported peaks can vary by about ±0.2°.

In some embodiments, the crystalline form of 4-(2-(4-(3-methoxybenzamido)-2-(1-methyl-1H-pyrazol-5-yl)phenoxy)ethyl)morpholin-4-ium chloride (Form I) has a differential scanning calorimetry trace comprising an endotherm at about 218° C. In further embodiments, the crystalline form has a differential scanning calorimetry trace substantially as shown in FIG. 2, wherein by "substantially" is meant that the reported DSC features can vary by about ±4°.

In some embodiments, the crystalline form of 4-(2-(4-(3-methoxybenzamido)-2-(1-methyl-1H-pyrazol-5-yl)phenoxy)ethyl)morpholin-4-ium chloride (Form I) has a crystal habit which is plate-like.

Figure 4:
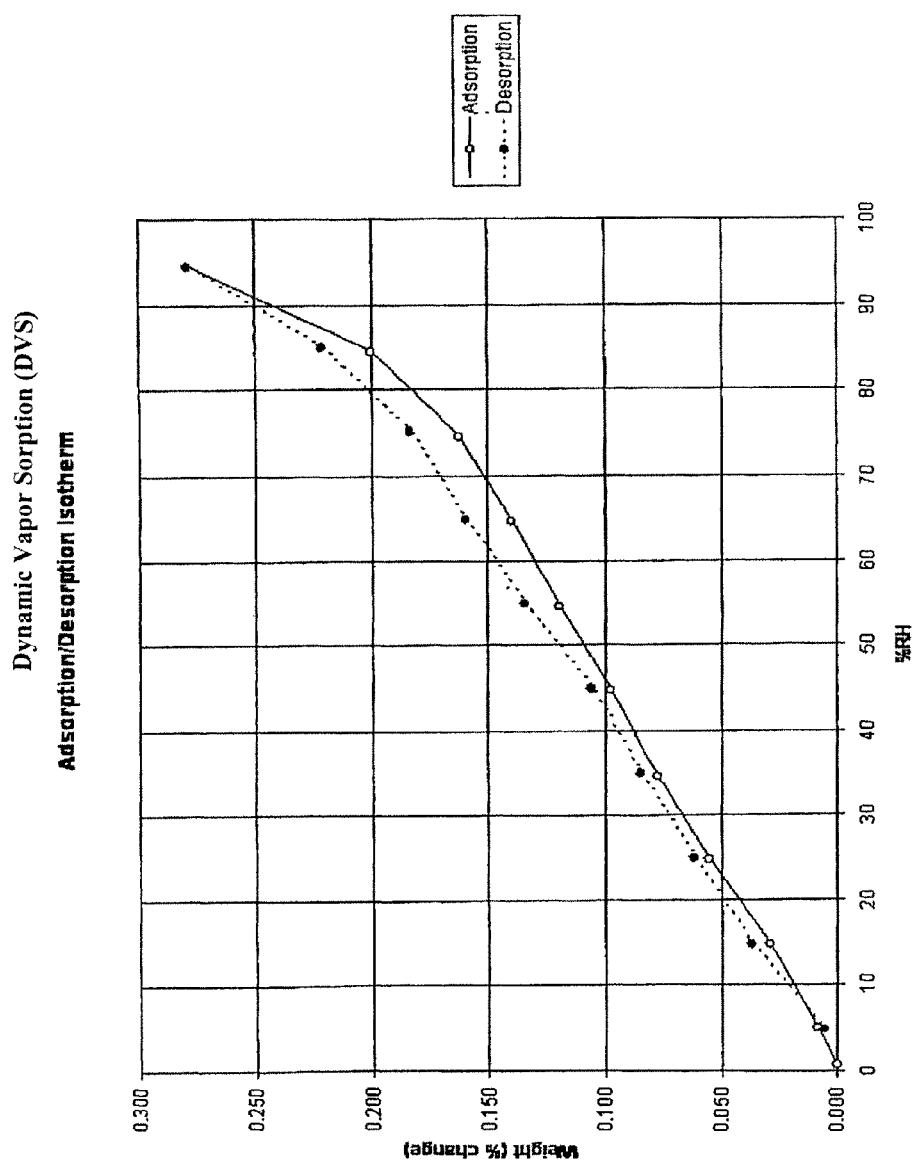
FIG. 4 depicts a dynamic vapor sorption (DVS) scan for crystalline Form I of Compound 7 of the invention (VTI dynamic vapor sorption analyzer).

In some embodiments, the crystalline form of 4-(2-(4-(3-methoxybenzamido)-2-(1-methyl-1H-pyrazol-5-yl)phenoxy)ethyl)morpholin-4-ium chloride (Form I) has a dynamic vapor sorption profile substantially as shown in FIG. 4, wherein by "substantially" is meant that the reported DVS features can vary by about ±5% RH.

Figure 2:
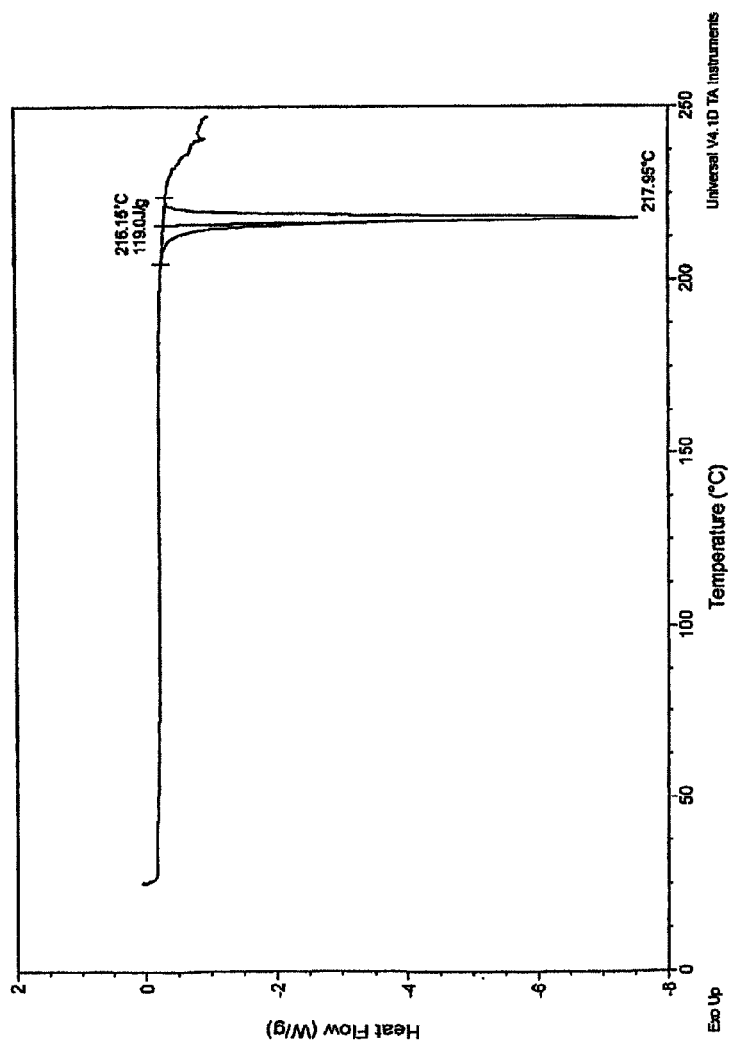
FIG. 2 depicts a differential scanning calorimetry (DSC) thermogram for crystalline Form I of Compound 7 of the invention (TA Instruments DSC Q1000; 25-250° C.; 10° C./min).

In some embodiments, the crystalline form of 4-(2-(4-(3-methoxybenzamido)-2-(1-methyl-1H-pyrazol-5-yl)phenoxy)ethyl)morpholin-4-ium chloride (Form I) has a thermogravimetric analysis profile substantially as shown in FIG. 1, wherein by "substantially" is meant that the reported TGA features can vary by about ±5° C.

Compound 7 Form I can be prepared by any of the suitable procedures known in the art for preparing crystalline polymorphs. In some embodiments Form I can be prepared as described in Example 6. In some embodiments Compound 7 Form I can be prepared as described in Example 12. In some embodiments, Compound 7 Form I can be prepared by heating crystalline 4-(2-(4-(3-methoxybenzamido)-2-(1-methyl-1H-pyrazol-5-yl)phenoxy)ethyl)morpholin-4-ium chloride, where the crystalline 4-(2-(4-(3-methoxybenzamido)-2-(1-methyl-1H-pyrazol-5-yl)phenoxy)ethyl)morpholin-4-ium chloride contains one or more crystalline forms other than Form I. In some embodiments, Compound 7 Form I can be prepared by recrystallizing crystalline 4-(2-(4-(3-methoxybenzamido)-2-(1-methyl-1H-pyrazol-5-yl)phenoxy)ethyl)morpholin-4-ium chloride, where the crystalline 4-(2-(4-(3-methoxybenzamido)-2-(1-methyl-1H-pyrazol-5-yl)phenoxy)ethyl)morpholin-4-ium chloride contains one or more crystalline forms other than Form I.

Compound 9 Form I

Figure 7:
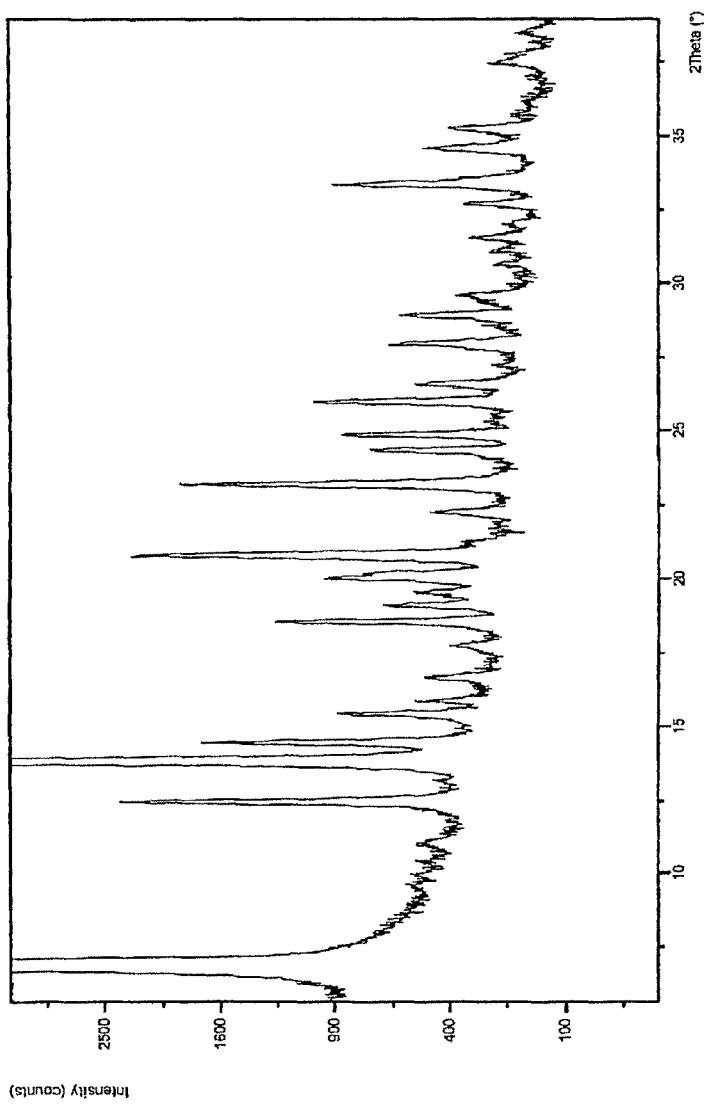
FIG. 7 depicts a powder X-ray diffraction pattern (XRPD) for a sample containing crystalline Form I of Compound 9 (PANalytical X'Pert Plus Powder X-Ray Diffractometer; 5.0°-40.0° 2θ).

One aspect of the present invention is directed to a crystalline form of 4-acetyl-1-(2-(4-(3-fluorobenzamido)-2-(1-methyl-1H-pyrazol-5-yl)phenoxy)ethyl)piperazin-1-ium carboxyformate (Form I) having an X-ray powder diffraction pattern comprising a peak, in terms of 2θ, at about 7.0°. In some embodiments, the crystalline form has an X-ray powder diffraction pattern comprising a peak, in terms of 2θ, at about 13.9°. In some embodiments, the crystalline form has an X-ray powder diffraction pattern comprising peaks, in terms of 2θ, at about 7.0° and about 12.5°. In some embodiments, the crystalline form has an X-ray powder diffraction pattern comprising peaks, in terms of 2θ, at about 13.9° and about 12.5°. In some embodiments, the crystalline form has an X-ray powder diffraction pattern comprising peaks, in terms of 2θ, at about 7.0°, about 13.9°, and about 12.5°. In some embodiments, the crystalline form has an X-ray powder diffraction pattern comprising peaks, in terms of 2θ, at about 7.0°, about 13.9°, about 12.5°, about 20.9°, about 23.2°, about 14.5°, and about 18.6°. In further embodiments, the crystalline form has an X-ray powder diffraction pattern comprising peaks, in terms of 2θ, at about 7.0°, about 13.9°, about 12.5°, about 20.9°, about 23.2°, about 14.5°, about 18.6°, about 26.0°, and about 33.4°. In yet further embodiments, the crystalline form has an X-ray powder diffraction pattern substantially as shown in FIG. 7, wherein by "substantially" is meant that the reported peaks can vary by about ±0.2°.

Figure 6:
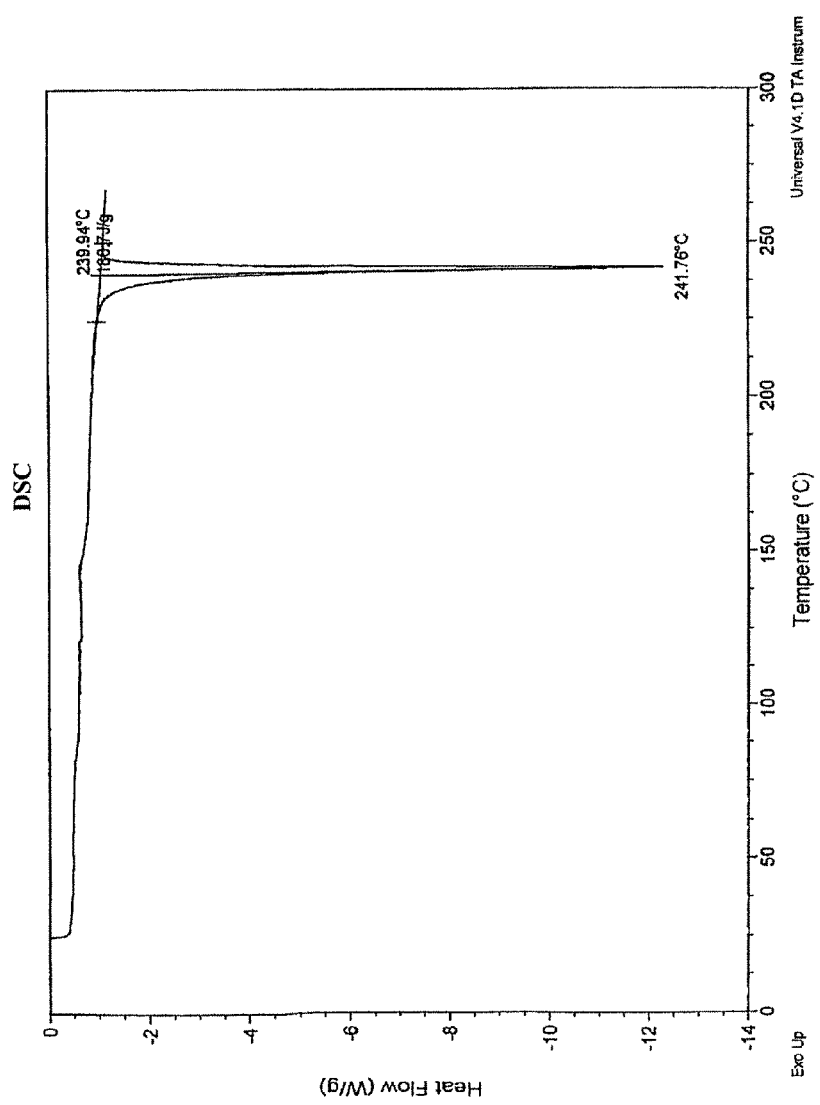
FIG. 6 depicts a differential scanning calorimetry (DSC) thermogram for crystalline Form I of Compound 9 of the invention (TA Instruments DSC Q1000; 25-270° C.; 10° C./min).

In some embodiments, the crystalline form of 4-acetyl-1-(2-(4-(3-fluorobenzamido)-2-(1-methyl-1H-pyrazol-5-yl)phenoxy)ethyl)piperazin-1-ium carboxyformate (Form 1) has a differential scanning calorimetry trace comprising an endotherm at about 240° C. In further embodiments, the crystalline form has a differential scanning calorimetry trace substantially as shown in FIG. 6, wherein by "substantially" is meant that the reported DSC features can vary by about ±4°.

Figure 8:
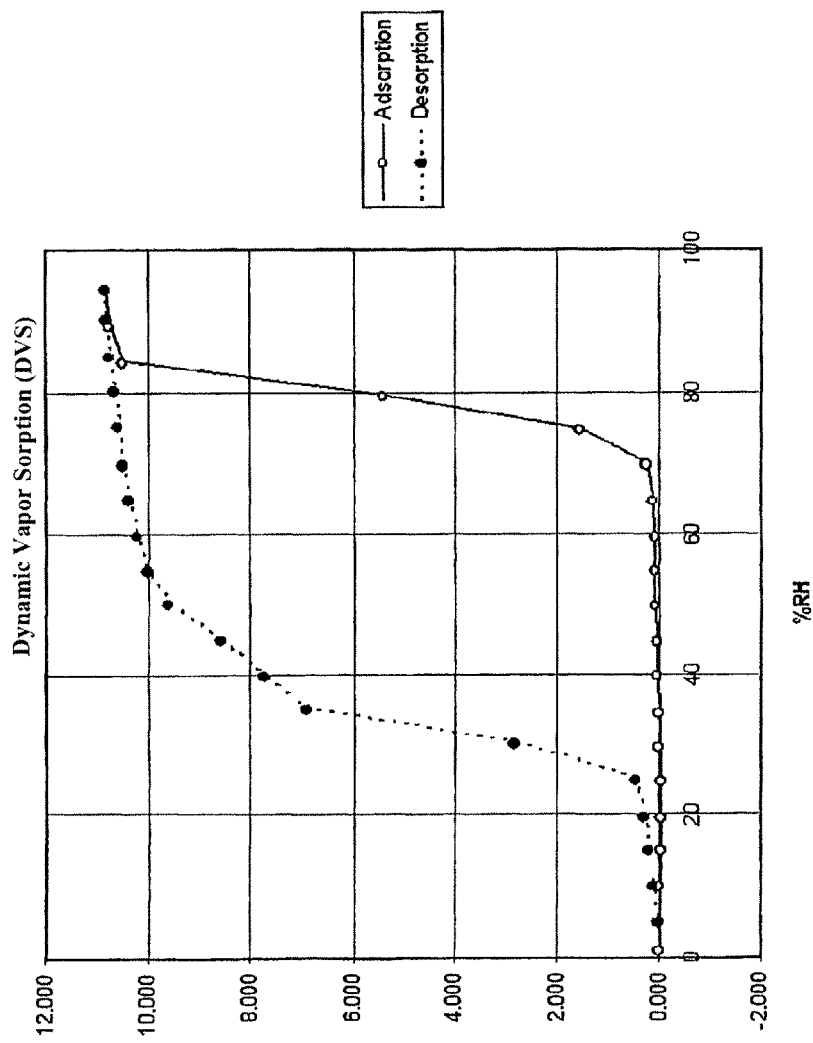
FIG. 8 depicts a dynamic vapor sorption (DVS) scan for crystalline Form I Compound 9 of the invention (VTI dynamic vapor sorption analyzer).

In some embodiments, the crystalline form of 4-acetyl-1-(2-(4-(3-fluorobenzamido)-2-(1-methyl-1H-pyrazol-5-yl)phenoxy)ethyl)piperazin-1-ium carboxyformate (Form I) has a dynamic vapor sorption profile substantially as shown in FIG. 8, wherein by "substantially" is meant that the reported DVS features can vary by about ±5% RH.

Figure 5:
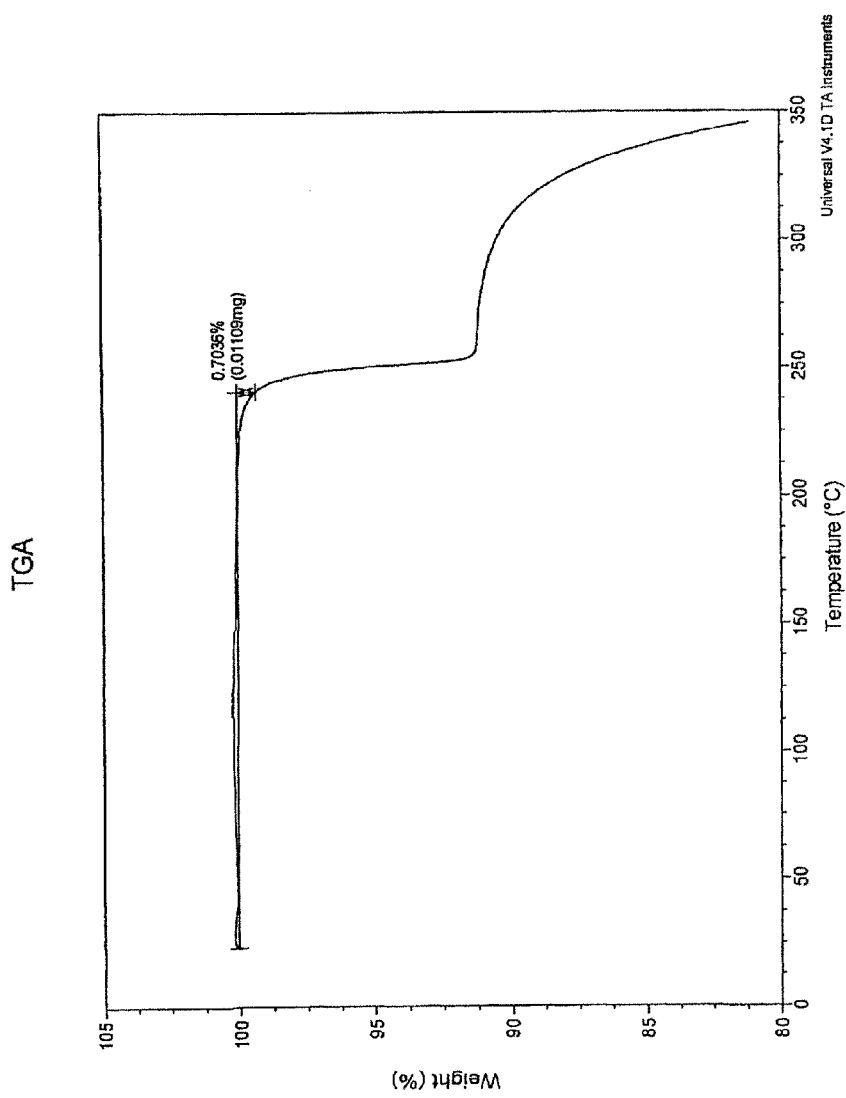
FIG. 5 depicts a thermogravimetric analysis (TGA) thermogram for crystalline Form I of Compound 9 the invention (TA Instruments TGA Q500 in open cell; 25-350° C.; 10° C./min).

In some embodiments, the crystalline form of 4-acetyl-1-(2-(4-(3-fluorobenzamido)-2-(1-methyl-1H-pyrazol-5-yl)phenoxy)ethyl)piperazin-1-ium carboxyformate (Form I) has a thermogravimetric analysis profile substantially as shown in FIG. 5, wherein by "substantially" is meant that the reported TGA features can vary be about ±5° C.

Compound 9 Form I can be prepared by any of the suitable procedures known in the art for preparing crystalline polymorphs. In some embodiments Compound 9 Form I can be prepared as described in Example 8. In some embodiments, Compound 9 Form I can be prepared by heating crystalline 4-acetyl-1-(2-(4-(3-fluorobenzamido)-2-(1-methyl-1H-pyrazol-5-yl)phenoxy)ethyl)piperazin-1-ium carboxyformate, where the crystalline 4-acetyl-1-(2-(4-(3-fluorobenzamido)-2-(1-methyl-1H-pyrazol-5-yl)phenoxy)ethyl)piperazin-1-ium carboxyformate contains one or more crystalline forms other than Form I. In some embodiments, Compound 9 Form I can be prepared by recrystallizing crystalline 4-acetyl-1-(2-(4-(3-fluorobenzamido)-2-(1-methyl-1H-pyrazol-5-yl)phenoxy)ethyl)piperazin-1-ium carboxyformate, where the crystalline 4-acetyl-1-(2-(4-(3-fluorobenzamido)-2-(1-methyl-1H-pyrazol-5-yl)phenoxy)ethyl)piperazin-1-ium carboxyformate contains one or more crystalline forms other than Form I.

Compositions

The present invention further provides compositions containing Form I of 4-(2-(4-(3-methoxybenzamido)-2-(1-methyl-1H-pyrazol-5-yl)phenoxy)ethyl)morpholin-4-ium chloride.

In some embodiments, the compositions of the invention include at least about 1, about 5, about 10, about 2θ, about 30, or about 40% by weight of Compound 7 Form L In some embodiments, the compositions of the invention include at least about 50, about 60, about 70, about 80, about 90, about 95, about 96, about 97, about 98, or about 99% by weight of Compound 7 Form I.

In some embodiments, compositions of the invention include Compound 7 Form I and a pharmaceutically acceptable carrier.

The present invention further provides compositions containing Form I of 4-acetyl-1-(2-(4-(3-fluorobenzamido)-2-(1-methyl-1H-pyrazol-5-yl)phenoxy)ethyl)piperazin-1-ium carboxyformate.

In some embodiments, the compositions of the invention include at least about 1, about 5, about 10, about 20, about 30, or about 40% by weight of Compound 9 Form I.

In some embodiments, the compositions of the invention include at least about 50, about 60, about 70, about 80, about 90, about 95, about 96, about 97, about 98, or about 99% by weight of Compound 9 Form I.

In some embodiments, compositions of the invention include Compound 9 Form I and a pharmaceutically acceptable carrier.

Methods

The crystalline forms and salts of the invention have activity as $5\text{-HT}_{2A}$ receptor modulators. Accordingly, crystalline forms or salts of the invention can be used in methods of modulating the $5\text{-HT}_{2A}$ receptor by contacting the receptor with a crystalline form or a salt, or compositions thereof, described herein. In further embodiments, a crystalline form or a salt of the invention can be used to modulate $5\text{-HT}_{2A}$ receptors in an individual in need of such modulation by administering a therapeutically effective amount of a crystalline form or a salt of the invention.

The present invention further provides methods of treating diseases associated with the $5\text{-HT}_{2A}$ receptor in an individual (e.g., patient) by administering to the individual in need of such treatment a therapeutically effective amount or dose of a salt or a crystalline form of the present invention or a pharmaceutical composition thereof. Example diseases can include any disease, disorder or condition that is directly or indirectly linked to expression or activity of the $5\text{-HT}_{2A}$ receptor.

Example diseases include platelet aggregation, coronary artery disease, myocardial infarction, transient ischemic attack, angina, stroke, atrial fibrillation, blood clot formation, asthma or symptoms thereof, agitation or a symptom thereof, behavioral disorders, drug induced psychosis, excitative psychosis, Gilles de la Tourette's syndrome, manic disorder, organic or NOS psychosis, psychotic disorder, psychosis, acute schizophrenia, chronic schizophrenia, NOS schizophrenia and related disorders, sleep disorders, diabetic-related disorders, progressive multifocal leukoencephalopathy, and the like The present invention further provides methods of treating coronary artery disease, myocardial infarction, transient ischemic attack, angina, stroke, and atrial fibrillation comprising administering to a patient in need thereof a therapeutically effective amount of a salt or a crystalline form of the invention.

The present invention further provides methods of treating a condition associated with platelet aggregation comprising administering to a patient in need thereof a therapeutically effective amount of a salt or a crystalline form of the invention.

The present invention further provides methods of reducing the risk of blood clot formation in an angioplasty or coronary bypass surgery individual comprising administering to a patient in need thereof a therapeutically effective amount of a salt or a crystalline form of the invention.

The present invention further provides methods of reducing the risk of blood clot formation in an individual suffering from atrial fibrillation comprising administering to a patient a therapeutically effective amount of a salt or a crystalline form of the invention.

The present invention further provides methods of treating a sleep disorder comprising administering to a patient a therapeutically effective amount of a salt or a crystalline form as described herein.

The present invention further provides methods of treating a dyssomnia comprising administering to a patient a therapeutically effective amount of a salt or a crystalline form as described herein.

The present invention further provides methods of treating a parasomnia comprising administering to a patient a therapeutically effective amount of a salt or a crystalline form as described herein.

The present invention further provides methods of treating a diabetic-related disorder comprising administering to a patient a therapeutically effective amount of a salt or a crystalline form as described herein.

The present invention further provides methods of treating progressive multifocal leukoencephalopathy comprising administering to a patient a therapeutically effective amount of a salt or a crystalline form as described herein.

The present invention further provides methods of treating hypertension comprising administering to a patient a therapeutically effective amount of a salt or a crystalline form as described herein.

The present invention further provides methods of treating pain comprising administering to a patient a therapeutically effective amount of a salt or a crystalline form as described herein.

In some embodiments, the above methods further comprise the step of identifying a patient, where the patient is in need of treatment for the particular disease being treated, wherein the identifying step is performed prior to administration to the patient of the therapeutically effective amount of a salt or a crystalline form as described herein.

One aspect of the present invention pertains to use of a salt or a crystalline form of the present invention for use in a method of treatment of the human or animal body by therapy.

One aspect of the present invention pertains to use of a salt or a crystalline form of the present invention for use in a method of treatment of a $5HT_{2A}$-related disorder of the human or animal body by therapy.

One aspect of the present invention pertains to use of a salt or a crystalline form of the present invention in a method of treatment of platelet aggregation, coronary artery disease, myocardial infarction, transient ischemic attack, angina, stroke, atrial fibrillation, blood clot formation, asthma or symptoms thereof, agitation or a symptom thereof, behavioral disorders, drug induced psychosis, excitative psychosis, Gilles de la Tourette's syndrome, manic disorder, organic or NOS psychosis, psychotic disorder, psychosis, acute schizophrenia, chronic schizophrenia, NOS schizophrenia and related disorders, sleep disorders, diabetic-related disorders or progressive multifocal leukoencephalopathy in the human or animal body by therapy.

One aspect of the present invention pertains to use of a salt or a crystalline form of the present invention for use in a method of treatment of coronary artery disease, myocardial infarction, transient ischemic attack, angina, stroke or atrial fibrillation in the human or animal body by therapy.

One aspect of the present invention pertains to use of a salt or a crystalline form of the present invention for use in a method for treating a condition associated with platelet aggregation in the human or animal body by therapy.

One aspect of the present invention pertains to use of a salt or a crystalline form of the present invention for use in a method for reducing the risk of blood clot formation in an angioplasty or coronary bypass surgery individual by therapy.

One aspect of the present invention pertains to use of a salt or a crystalline form of the present invention for use in a method for reducing the risk of blood clot formation in an individual suffering from atrial fibrillation by therapy.

One aspect of the present invention pertains to use of a salt or a crystalline form of the present invention for use in a method for treating a sleep disorder in the human or animal body by therapy.

One aspect of the present invention pertains to use of a salt or a crystalline form of the present invention for use in a method for treating a parasomnia in the human or animal body by therapy.

One aspect of the present invention pertains to use of a salt or a crystalline form of the present invention for use in a method for treating a dyssomnia in the human or animal body by therapy.

One aspect of the present invention pertains to use of a salt or a crystalline form of the present invention for use in a method for treating a diabetic-related disorder in the human or animal body by therapy.

One aspect of the present invention pertains to use of a salt or a crystalline form of the present invention for use in a method for treating progressive multifocal leukoencephalopathy in the human or animal body by therapy.

One aspect of the present invention pertains to use of a salt or a crystalline form of the present invention for use in a method for treating hypertension in the human or animal body by therapy.

One aspect of the present invention pertains to use of a salt or a crystalline form of the present invention for use in a method for treating pain in the human or animal body by therapy.

One aspect of the present invention pertains to use of a salt or a crystalline form of the present invention for the manufacture of a medicament for treating a $5HT_{2A}$-related disorder.

One aspect of the present invention pertains to use of a salt or a crystalline form of the present invention for the manufacture of a medicament for treating platelet aggregation, coronary artery disease, myocardial infarction, transient ischemic attack, angina, stroke, atrial fibrillation, blood clot formation, asthma or symptoms thereof, agitation or a symptom thereof, behavioral disorders, drug induced psychosis, excitative psychosis, Gilles de la Tourette's syndrome, manic disorder, organic or NOS psychosis, psychotic disorder, psychosis, acute schizophrenia, chronic schizophrenia, NOS schizophrenia and related disorders, sleep disorders, diabetic-related disorders, progressive multifocal leukoencephalopathy.

One aspect of the present invention pertains to use of a salt or a crystalline form of the present invention for the manufacture of a medicament for treating coronary artery disease, myocardial infarction, transient ischemic attack, angina, stroke, and atrial fibrillation.

One aspect of the present invention pertains to use of a salt or a crystalline form of the present invention for the manufacture of a medicament for treating condition associated with platelet aggregation.

One aspect of the present invention pertains to use of a salt or a crystalline form of the present invention for the manufacture of a medicament for reducing the risk of blood clot formation in an angioplasty or coronary bypass surgery individual.

One aspect of the present invention pertains to use of a salt or a crystalline form of the present invention for the manufacture of a medicament for reducing the risk of blood clot formation in an individual suffering from atrial fibrillation.

One aspect of the present invention pertains to use of a salt or a crystalline form of the present invention for the manufacture of a medicament for treating a sleep disorder.

One aspect of the present invention pertains to use of a salt or a crystalline form of the present invention for the manufacture of a medicament for treating a dyssomnia.

One aspect of the present invention pertains to use of a salt or a crystalline form of the present invention for the manufacture of a medicament for treating a parasomnia.

One aspect of the present invention pertains to use of a salt or a crystalline form of the present invention for the manufacture of a medicament for treating a diabetic-related disorder.

One aspect of the present invention pertains to use of a salt or a crystalline form of the present invention for the manufacture of a medicament for treating progressive multifocal leukoencephalopathy.

One aspect of the present invention pertains to use of a salt or a crystalline form of the present invention for the manufacture of a medicament for treating hypertension.

One aspect of the present invention pertains to use of a salt or a crystalline form of the present invention for the manufacture of a medicament for treating pain.

As used herein, the term "treating" refers to, for example, preventing, inhibiting, as well as ameliorating a disease, condition or disorder in an individual.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) preventing the disease; for example, preventing a disease, condition or disorder in an individual that may be predisposed to the disease, condition or disorder but does not yet experience or display the pathology or symptomatology of the disease;

(2) inhibiting the disease; for example, inhibiting a disease, condition or disorder in an individual that is experiencing or displaying the pathology or symptomatology of the disease, condition or disorder (i.e., arresting further development of the pathology and/or symptomatology) such as stabilizing viral load in the case of a viral infection; and (3) ameliorating the disease; for example, ameliorating a disease, condition or disorder in an individual that is experiencing or displaying the pathology or symptomatology of the disease, condition or disorder (i.e., reversing the pathology and/or symptomatology) such as lowering viral load in the case of a viral infection.

Pharmaceutical Compositions

A further aspect of the present invention pertains to pharmaceutical compositions comprising one or more compounds as described herein and one or more pharmaceutically acceptable carriers. Some embodiments pertain to pharmaceutical compositions comprising a compound of the present invention and a pharmaceutically acceptable carrier. Some embodiments pertain to pharmaceutical compositions comprising a salt of the present invention and a pharmaceutically acceptable carrier. Some embodiments pertain to pharmaceutical compositions comprising a crystal form of the present invention and a pharmaceutically acceptable carrier.

Some embodiments of the present invention include a method of producing a pharmaceutical composition comprising admixing at least one compound according to any of the compound embodiments disclosed herein and a pharmaceutically acceptable carrier.

Some embodiments of the present invention include a method of producing a pharmaceutical composition comprising admixing a salt disclosed herein and a pharmaceutically acceptable carrier.

Some embodiments of the present invention include a method of producing a pharmaceutical composition comprising admixing a crystal form disclosed herein and a pharmaceutically acceptable carrier.

Formulations may be prepared by any suitable method, typically by uniformly mixing the active compound(s) with liquids or finely divided solid carriers, or both, in the required proportions, and then, if necessary, forming the resulting mixture into a desired shape.

Conventional excipients, such as binding agents, fillers, acceptable wetting agents, tabletting lubricants, and disintegrants may be used in tablets and capsules for oral administration. Liquid preparations for oral administration may be in the form of solutions, emulsions, aqueous or oily suspensions, and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives, and flavorings and colorants may be added to the liquid preparations. Parenteral dosage forms may be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, *The Science and Practice of Pharmacy*, 20$^{th}$ Ed., 2000, Lippincott Williams & Wilkins, (Editors: Gennaro, A. R., et al.).

While it is possible that, for use in the treatment, a compound of the invention may, in an alternative use, be administered as a raw or pure chemical, it is preferable however to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt or derivative thereof together with one or more pharmaceutically acceptable carriers thereof and/or prophylactic ingredients. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof, and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active'compounds or principles, and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a solvate or physiologically functional derivative thereof can be used as active ingredients in pharmaceutical compositions, specifically as 5-$HT_{2A}$ receptor modulators. By the term "active ingredient" is defined in the context of a "pharmaceutical composition" and shall mean a component of a pharmaceutical composition that provides the primary pharmacological effect, as opposed to an "inactive ingredient" which would generally be recognized as providing no pharmaceutical benefit.

The dose when using the compounds of the present invention can vary within wide limits, as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds of the present invention. Representative doses of the present invention include, but are not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg, and about 0.001 mg to about 25 mg. Multiple doses may be administered during the day, especially when relatively large amounts are deemed to be needed, for example 2, 3 or 4, doses. Depending on the individual and as deemed appropriate from the patient's physician or care-giver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, or whether an acute or chronic disease state is being treated or prophylaxis is conducted or on whether further active compounds are administered in addition to the compounds of the present invention and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day.

The sub-dose itself may be further divided, e.g., into a number of discrete loosely spaced administrations. The daily dose can be divided, especially when relatively large amounts are administered as deemed appropriate, into several, for example 2, 3 or 4, part administrations. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffer's, artificial and natural sweeteners, dispersants, thickeners, solubilizing agents, and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well-known to the person skilled in the art. For their preparation, for example, solutions or dispersions of the compounds of the present invention in water, water/alcohol mixtures or suitable saline solutions can be employed using customary additives, for example benzyl alcohol or other suitable preservatives, absorption enhancers for increasing the bioavailability, solubilizers, dispersants and others, and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethylcellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself; or it can be the appropriate number of any of these in packaged form.

Tablets or capsules for oral administration and liquids for intravenous administration are preferred compositions.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

It is noted that when the $5\text{-HT}_{2A}$ receptor modulators are utilized as active ingredients in a pharmaceutical composition, these are not intended for use only in humans, but in other non-human mammals as well. Indeed, recent advances in the area of animal health-care mandate that consideration be given for the use of active agents, such as $5\text{-HT}_{2A}$ receptor modulators, for the treatment of a $5\text{-HT}_{2A}$ mediated disease or disorder in domestic animals (e.g., cats and dogs) and in other domestic animals (e.g., such as cows, chickens, fish, etc.). Those of ordinary skill in the art are readily credited with understanding the utility of such compounds in such settings.

Definitions

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, cyclohexenyl, and the like.

As used herein, "alkynyl" refers to an alkyl group having one or more triple carbon-carbon bonds. Example alkynyl groups include ethynyl, propynyl, and the like.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like. An alkyl group in which all of the hydrogen atoms are replaced with halogen atoms can be referred to as "perhaloalkyl."

As used herein, "aryl" refers to monocyclic or polycyclic aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic hydrocarbons including cyclized alkyl, alkenyl, and alkynyl groups. Cycloalkyl groups can include mono-, bi- or polycyclic ring systems as well as double and triple bonds. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, adamantyl, and the like. Also included in the definition of cycloalkyl are moieties that have one or more aromatic rings fused with (i.e., having a bond in common with) the cycloalkyl ring, for example, benzo derivatives of pentane, hexane, and the like.

As used herein, "heterobicyclyl" is intended to mean a bicyclic ring, as described herein, wherein 1, 2, or 3 ring carbons are replaced with a heteroatom or group selected from, but are not limited to, the group consisting of O, S, S(=O), S(=O)$_2$, and NH, wherein the nitrogen can be optionally substituted, and 1 or 2 ring carbons can be optionally substituted with oxo or thiooxo thus together forming a carbonyl or thiocarbonyl group respectively. In some embodiments, one of the rings is aromatic. Examples of a heterobicyclic group include, but are not limited to, 2,5-diaza-bicyclo[2.2.1]hept-2-yl, 7-aza-bicyclo[2.2.1]hept-7-yl, 1,3-dihydro-isoindolyl, 3,4-dihydro-1H-isoquinolinyl, octahydro-cyclopenta[c]pyrrolyl and the like As used herein, "heterocyclyl" refers to a group that can be a saturated or unsaturated carbocyclyl group wherein one or more of the ring-forming carbon atoms of the carbocyclyl group are replaced by a heteroatom such as O, S, or N. Heterocyclyl groups can be aromatic (e.g., "heteroaryl") or non-aromatic (e.g., "heterocycloalkyl"). Heterocyclyl groups can correspond to hydrogenated and partially hydrogenated heteroaryl groups. Heterocarbocyclyl groups can contain, in addition to at least one heteroatom, from about 1 to about 20, about 2 to about 10, or about 2 to about 7 carbon atoms and can be attached through a carbon atom or heteroatom. In some embodiments, heterocyclyl groups can have from 3 to 20, 3 to 10, 3 to 7, or 5 to 7 ring-forming atoms. Further, heterocyclyl groups can be substituted or unsubstituted. Examples of heterocyclyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like as well as any of the groups listed for heteroaryl and heterocycloalkyl.

As used herein, "heteroaryl" groups are monocyclic and polycyclic aromatic hydrocarbons that have at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrrolyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-5-oxide, 2,3-dihydrobenzothienyl-5-dioxide, benzoxazolin-2-on-yl, indolinyl, benzodioxolanyl, benzodioxane, and the like. In some embodiments, heteroaryl groups can have from 1 to about 20 carbon atoms, and in further embodiments from about 3 to about 20 carbon atoms. In some embodiments, heteroaryl groups have 1 to about 4, 1 to about 3, or 1 to 2 heteroatoms.

As used herein, "halo" or "halogen" includes fluoro, chloro, bromo, and iodo. As used herein, "alkoxy" refers to an —O-alkyl group. Example alkoxy groups include methoxy, ethoxy, propoxy (e.g., n-propoxy and isopropoxy), t-butoxy, and the like.

As used herein, "haloalkoxy" refers to alkoxy substituted by at least one halo.

As used herein, "acyl" refers to a carbonyl group substituted by H, alkyl, alkenyl, alkynyl or carbocyclyl. Example acyl groups include formyl or acetyl.

As used herein, "arylalkyl" refers to an alkyl moiety substituted by an aryl group. Example arylalkyl groups include benzyl, phenethyl, and naphthylmethyl groups. In some embodiments, arylalkyl groups have from 7 to 20 or 7 to 11 carbon atoms.

As used herein, "heterocycloalkyl" refers to alkyl substituted by heterocyclyl.

As used herein, "cycloalkylalkyl" refers to alkyl substituted by cycloalkyl.

As used herein, "heteroarylalkyl" refers to alkyl substituted by heteroaryl.

As used herein, the term "reacting" is used as known in the art and generally refers to the bringing together of chemical reagents in such a manner so as to allow their interaction at the molecular level to achieve a chemical or physical transformation of at least one chemical reagent.

As used herein, the term "substituted" refers to the replacement of a hydrogen moiety with a non-hydrogen moiety in a molecule or group.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

In some embodiments, preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis,* 3$^{rd}$ Ed., Wiley & Sons, 1999, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, or t-butyl methyl ether.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, tetrahydrofuran, N,N-dimethylformamide, N,N-dimethylacetamide, 1,3-dimethyl-3,4,5,6-tetrahydro-2(1H)-pyrimidinone, 1,3-dimethyl-2-imidazolidinone, N-methylpyrrolidinone, formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, o, m-, or p-xylene, octane, indane, nonane, or naphthalene.

Supercritical carbon dioxide can also be used as a solvent.

The reactions of the processes described herein can be carried out at appropriate temperatures which can be readily determined by one skilled in the art. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

The reactions of the processes described herein can be carried out in air or under an inert atmosphere. Typically, reactions containing reagents or products that are substantially reactive with air can be carried out using air-sensitive synthetic techniques that are well known to one skilled in the art.

In some embodiments, preparation of compounds can involve the addition of acids or bases to effect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, methanesulfonic acid, p-toluene sulfonic acid, benzenesulfonic acid, propiolic acid, butyric acid, 2-butynoic acid, vinyl acetic acid, pentanoic acid, hexanoic acid, heptanoic acid, octanoic acid, nonanoic acid and decanoic acid.

Example bases include lithium hydroxide, sodium hydroxide, potassium hydroxide, lithium carbonate, sodium carbonate, and potassium carbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis.

The processes described herein can be stereoselective such that any given reaction starting with one or more chiral reagents enriched in one stereoisomer forms a product that is also enriched in one stereoisomer. The reaction can be conducted such that the product of the reaction substantially retains one or more chiral centers present in the starting materials. The reaction can also be conducted such that the product of the reaction contains a chiral center that is substantially inverted relative to a corresponding chiral center present in the starting materials.

Resolution of racemic mixtures of compounds can be carried out by any of numerous methods known in the art. An example method includes fractional recrystallization (for example, diastereomeric salt resolution) using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of β-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention can also include all isotopes of atoms occurring in the intermediates or final compounds. Isotopes include those atoms having the same atomic number but different mass numbers. For example, isotopes of hydrogen include tritium and deuterium.

Compounds of the invention can also include tautomeric forms, such as keto-enol tautomers. Tautomeric forms can be in equilibrium or sterically locked into one form by appropriate substitution.

Upon carrying out preparation of compounds according to the processes described herein, the usual isolation and purification operations such as concentration, filtration, extraction, solid-phase extraction, recrystallization, chromatography, and the like may be used, to isolate the desired products.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

Preparation of 1-(4-hydroxy-3-(1-methyl-1H-pyrazol-5-yl)phenyl)ethanone (Compound 2)

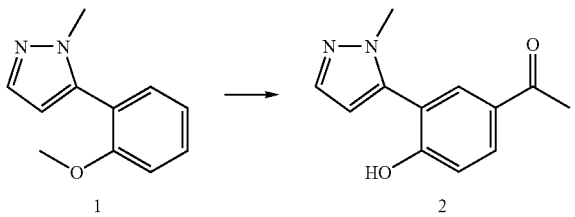 [SMILES: COc1ccccc1-c1ccnn1C ; CC(=O)c1ccc(O)c(-c2ccnn2C)c1]

To a stirred solution of 5-(2-methoxyphenyl)-1-methyl-1H-pyrazole (5.00 g, 26.56 mmol) in 1,2-dichlorobenzene (30 mL) was added acetyl chloride (3.13 g, 39.85 mmol) followed by aluminum chloride (10.63 g, 79.69 mmol). The reaction became amber-colored and was heated to 55° C. for 40 minutes. The temperature was increased to 80° C. and the reaction was stirred for a further 2 hours, after which a thick slurry was obtained. LCMS analysis showed conversion to 1-(4-hydroxy-3-(1-methyl-1H-pyrazol-5-yl)phenyl)ethanone and partial formation of the O-acylated analog. The reaction was cooled to room temperature and slowly quenched with water (50 mL) to form a precipitate. This was filtered, washed with water (30 mL) and heptane (50 mL) and dried in a vacuum oven (12 Torr) overnight at 60° C. to obtain compound (2) as a white solid (3.80 g, 66%). LCMS: m/z 217 (M+H)$^+$; $^1$H NMR. (DMSO-$d_6$) δ 11.0 (s, 1H), 7.92 (d, J=8 Hz, 1H) 7.79 (s, 1H), 7.46 (s, 1H), 7.10 (d, J=8 Hz, 1H), 6.30 (s, 1H), 3.67 (s, 3H), 2.51 (s, 3H).

Example 2a

Preparation of N-(4-methoxy-3-(1-methyl-1H-pyrazol-5-yl)phenyl)acetamide (Compound 3)

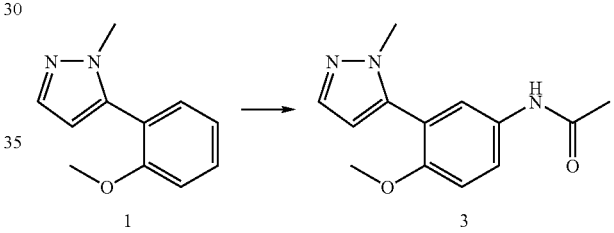

Polyphosphoric acid (15 g) was transferred to a 100 mL, 3-necked round bottomed flask fitted with a mechanical stirrer. A solution of 5-(2-methoxyphenyl)-1-methyl-1H-pyrazole (1.50 g, 7.97 mmol) in acetic acid (9.57 g, 9.12 mL, 15.9 mmol) was transferred into the reaction flask followed by hydroxylamine hydrochloride (6.08 g, 8.75 mmol). The mixture was stirred under nitrogen and heated to 80° C. for 3.5 hours. Acetic acid (1 mL) and hydroxylamine hydrochloride (0.61 g) were added and the reaction was stirred at 80° C. for a further 2 hours. The reaction was then heated to 100° C. and stirred overnight. Additional amounts of acetic acid (1 mL) and hydroxylamine hydrochloride (0.61 g) were added and the stirring at 100° C. was continued for a further 1 hour. The reaction was then cooled to room temperature and diluted with ice-cold water (40 mL) with cooling in an ice bath. The pH was adjusted to 5 by the addition of 50% aqueous NaOH to form a precipitate. The solid was isolated by filtration and the cake was washed with water. The crude material was purified by crystallization from methanol-water to obtain compound (3) (1.00 g, 51%). LCMS: m/z 246 (M+H)$^+$; $^1$H NMR (DMSO-$d_6$): δ 9.9 (s, 1H), 7.62 (dd, $J_1$=8 Hz, $J_2$=4 Hz, 1H), 7.49 (d, J=4 Hz, 1H), 7.43 (s, 1H), 7.10 (d, J=8 Hz, 1H), 6.22 (d, J=4 Hz, 1H), 3.75 (s, 3H), 3.61 (s, 3H), 2.01 (s, 3H).

Example 2b

Preparation of N-(4-methoxy-3-(1-methyl-1H-pyrazol-5-yl)phenyl)acetamide (Compound 3)

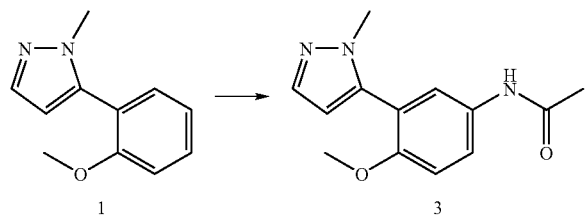 [SMILES: COc1ccccc1-c1ccnn1C ; COc1ccc(NC(C)=O)cc1-c1ccnn1C]

To a solution of 5-(2-methoxyphenyl)-1-methyl-1H-pyrazole (2.00 g, 10.62 mmol) in acetic acid (127 g, 121 mL, 2125 mmol) was added phosphorus pentoxide (7.7 wt. % in methanesulfonic acid, 20 mL) and the solution was stirred at 60° C. for 15 minutes. A second batch of acetic acid (1.27 g) was added and the reaction was stirred at 60° C. for 10 minutes. Hydroxylamine hydrochloride (1.47 g, 21.25 mmol) was added and the reaction was stirred for 40 minutes. Another batch of hydroxylamine hydrochloride (1.47 g, 21.25 mmol) was added and the reaction was stirred at 60° C. for a further 10 minutes. The reaction was cooled to room temperature, ice cold water (50 mL) was added with cooling in an ice bath and the mixture was basified to pH 5 by the addition of 50% aqueous NaOH: A gummy precipitate formed, which gradually solidified. This was filtered and the cake was washed with water. The product was crystallized from methanol-water to leave compound (3) (1.23 g, 50%). LCMS: m/z 246 (M+H)$^+$; $^1$H NMR (DMSO-d$_6$) δ 9.9 (s, 1H), 7.61 (dd, J=8 Hz, J$_2$=Hz, 1H), 7.49 (d, J=4 Hz, 1H), 7.43 (s, 1H), 7.09 (d, J=8 Hz, 1H), 6.21 (s, 1H), 3.75 (s, 3H), 3.61 (s, 3H), 2.01 (s, 3H).

Example 3a

Preparation of N-(4-hydroxy-3-(1-methyl-1H-pyrazol-5-yl)phenyl)acetamide (Compound 4)

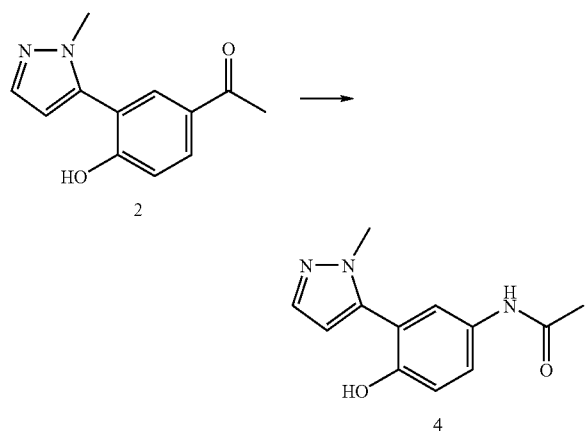

A slurry of 1-(4-hydroxy-3-(1-methyl-1H-pyrazol-5-yl)phenyl)ethanone (2.50 g, 11.56 mmol) in acetic acid (12.5 mL) was stirred at 70° C. to obtain a clear solution. Hydroxylamine hydrochloride (1.60 g, 23.02 mmol) was added followed by H$_2$SO$_4$ (98%, 1.25 mL). The temperature was increased to 80° C. and the reaction was stirred for 30 minutes. LCMS analysis showed formation of the oxime intermediate while the starting material was not detected. H$_2$SO$_4$ (98%, 5 mL) was added and the reaction was stirred at 80° C. for 30 minutes. Additional H$_2$SO$_4$ (2 mL) was added in two portions over 2 hours, after which the reaction was stirred and heated at 80° C. for a further 4 hours. Additional amount of H$_2$SO$_4$ (98%, 0.5 mL) was added and the reaction was stirred and heated at 80° C. for a further 30 minutes. The reaction was then cooled to room temperature, and poured into ice-water (80 mL). The mixture was basified to pH 4-5 by the addition of aqueous NaOH (50%) with cooling in an ice bath. The product crystallized out and was filtered, washed with water and dried to give compound (4) as an off-white powder (1.83 g, 68%). LCMS: m/z 232.4 (M+H)$^+$; $^1$H NMR (DMSO-d$_6$): δ 9.79 (s, 1H), 9.68 (s, 1H), 7.42 (m, 3H), 6.99 (d, J=8 Hz, 1H), 6.20 (d, J=4 Hz, 1H), 3.66 (s, 3H), 1.99 (s, 3H).

Example 3b

Preparation of N-(4-hydroxy-3-(1-methyl-1H-pyrazol-5-yl)phenyl)acetamide (Compound 4)

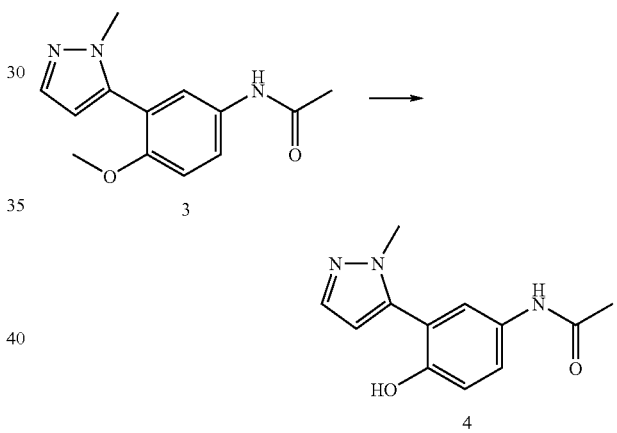

Under a nitrogen atmosphere N,N-dimethylacetamide (13.47 kg) was transferred into a 30 L jacketed reaction vessel and 1-dodecanethiol (4.894 kg, 24.18 mol) was added with stirring followed by portionwise addition of sodium ethoxide (1.63 kg, 23.97 mol) over 1 hour. The reaction temperature reached to 41° C. due to a mild exotherm. The temperature was gradually increased to 63° C. and N-(4-methoxy-3-(1-methyl-1H-pyrazol-5-yl)phenyl)acetamide (3.504 kg, 14.29 mol) was added and the reaction was heated up to 135-136° C. and stirred overnight at which point LCMS analysis showed no starting material remained. The reaction mixture was concentrated by distillation of the solvent under reduced pressure. Water (14.41 kg) was added to the reaction with stirring. HCl (37%) was added in portions to adjust the reaction pH to 3 and the product crystallized out. The slurry was filtered and the solid cake was washed with water (2×6.56 kg) followed by heptane (2×5.374 kg). The dried solid cake (3.26 kg) was re-slurried in heptane (10.92 kg) and the slurry was refluxed for 1 hour. A portion of the heptane was removed by distillation, which azeotropically removed residual water in the product. The suspension was cooled to 20° C. and filtered.

The solid cake was washed with heptane and dried to obtain compound (4) (3.09 kg, 93%). LCMS; m/z 232 (M+H).

Example 4

Preparation of 4-amino-2-(1-methyl-1H-pyrazol-5-yl)phenol (Compound 5)

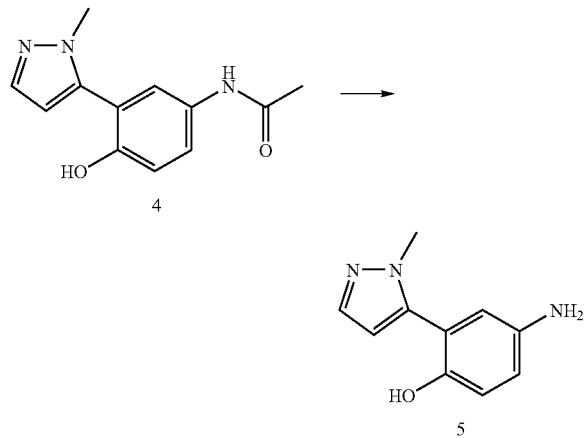

A stirred slurry of N-(4-hydroxy-3-(1-methyl-1H-pyrazol-5-yl)phenyl)acetamide (1.77 g, 7.65 mmol) in methanol (7.0 mL) was warmed (45-50° C.) to obtain a clear solution. $H_2SO_4$ (98%, 1.22 mL) was added slowly to the reaction mixture, which was then heated to reflux for 5.5 hours. The reaction was cooled to room temperature and the solvent was removed under reduced pressure. The residue was diluted with water (10 mL), neutralized to pH 7 by the addition of aqueous NaOH (50%), and then basified to pH 8 with saturated aqueous $NaHCO_3$. The product crystallized out and was filtered and dried to afford the compound (5) (1.13 g, 78%). LCMS: m/z 190.2 (M+H)$^+$; $^1$H NMR (DMSO-d$_6$): δ 8.85 (s, 1H), 7.38 (s, 1H), 6.69 (d, J=8 Hz, 1H), 6.54 (dd, J=8 Hz, J$_2$=4 Hz, 1H), 6.43 (s, 1H), 6.13 (d, J=4 Hz, 1H), 4.79 (s, 2H), 3.65 (s, 3H).

Example 5

Preparation of N-(4-hydroxy-3-(1-methyl-1H-pyrazol-5-yl)phenyl)-3-methoxybenzamide (Compound 6)

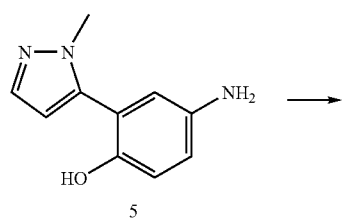

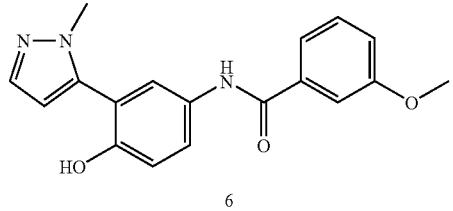

To a stirred solution of 4-amino-2-(1-methyl-1H-pyrazol-5-yl)phenol (1.08 g, 5.71 mmol) in N,N-dimethylacetamide (6.5 mL) was added $NaHCO_3$ (0.48 g, 5.08 mmol) and the mixture was cooled to −10° C. 3-Methoxybenzoyl chloride (0.82 mL, 6.00 mmol) was added dropwise and on completion of the addition the reaction was stirred at −10° C. for a further 15 minutes and then at room temperature for 1 hour. Water (16.2 mL) was added dropwise and the product crystallized out and was isolated by filtration. The solid cake was washed with 10% aqueous $NaHCO_3$ (2×20 mL) followed by water and then dried to obtain the compound (6) (1.66 g, 90%). LCMS: m/z 324.3 (M+H)$^+$; $^1$H NMR (DMSO-d$_6$): δ 10.11 (s, 1H), 9.80 (s, 1H), 7.64 (d, J=8 Hz, 1H), 7.60 (d, J=4 Hz, 1H), 7.51 (d, J=8 Hz, 1H), 7.47 (t, J=4 Hz, 1H), 7.44 (m, 2H), 7.14 (d, J=8 Hz, 1H), 6.96 (d, J=8 Hz, 1H), 6.24 (s, 1H), 3.83 (s, 3H), 3.70 (s, 3H).

Example 6

Preparation of 4-(2-(4-(3-methoxybenzamido)-2-(1-methyl-1H-pyrazol-5-yl)phenoxy)ethyl)morpholin-4-ium chloride (Compound 7)

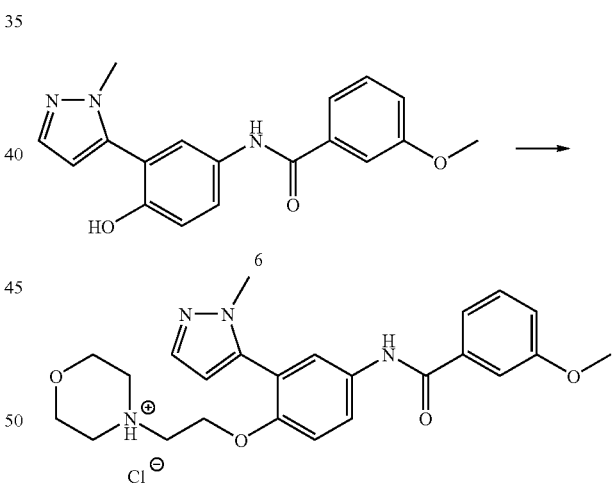

To a stirred solution of N-(4-hydroxy-3-(1-methyl-1H-pyrazol-5-yl)phenyl)-3-methoxybenzamide (22.2 g, 0.069 mol) in THF (246 mL) was added triphenylphosphine (27.0 g, 0.103 mol). The solution was cooled to −15° C. and diisopropyl azodicarboxylate (20.8 g, 0.103 mol) was added dropwise. On completion of the addition, the mixture was warmed to 5° C. and 2-morpholinoethanol (13.5 g, 0.092 mol) was added dropwise while maintaining the internal temperature below 10° C. On completion of the addition, the reaction was allowed to warm to room temperature. The reaction was complete after 30 minutes at which point the THF was removed by distillation and the residue was dissolved in isopropanol (225 mL). The solution was heated to 70° C. with stirring; HCl (37%, 9.9 mL, 0.119 mol) was added in portions while maintaining the internal reaction temperature between 70 and 80° C. The HCl salt of the product crystallized out on gradual cooling to room temperature. The solids were filtered, washed with isopropanol and dried to leave compound (7) (26.0 g, 80%).

A stirred solution of N-(4-hydroxy-3-(1-methyl-1H-pyrazol-5-yl)phenyl)-3-methoxybenzamide (11.7 kg, containing 5.2% water, 34.3 mol) in THF (107 kg) was distilled at atmospheric pressure to remove approximately 70-80% of the solvent. THF (99 kg) was added followed by triphenylphosphine (14.14 kg, 53.91 mol). The solution was cooled to −12° C. and diisopropyl azodicarboxylate (11.02 kg, 52.5 mol) was added in portions while maintaining the internal temperature between −10° C. and 0° C. On completion of the addition, the mixture was stirred at −10° C. to 3° C. for 40 minutes. 2-Morpholinoethanol (7.10 kg, 54.13 mol) was added in portions at 2-6° C. On completion of the addition, the reaction was warmed to room temperature and stirred for 4 hours. Approximately 70-80% of the THF was removed by distillation and isopropanol (92 kg) was added. A further 111 kg of the solvent mixture was removed by distillation and isopropanol (109 kg) was added. HCl (37%, 5.70 kg, 57.8 mol) was added in portions while maintaining the internal reaction temperature between 60 and 70° C. The HCl salt of the product crystallized out on cooling to room temperature. The solids were filtered, washed with isopropanol and dried to leave compound (7) (14.53 kg, 90%). LCMS: m/z 437 (M+H)$^+$; NMR. (DMSO-d$_6$) δ 11.3 (bs, 1H), 10.32 (s, 1H), 7.91 (dd, J$_1$=8 Hz, J$_2$=4 Hz, 1H), 7.75 (d, J=4 Hz, 1H), 7.54 (d; J=8 Hz, 1H), 7.49 (m, 2H, 1H), 7.44 (t, J=8 Hz, 1H), 7.24 (d, J=8 Hz, 1H), 7.16 (dd, J=8 Hz, J$_2$=4 Hz, 1H), 6.29 (d, J=4 Hz, 1H), 4.46 (t, J=4 Hz, 2H), 3.83 (s, 3H), 3.82-3.70 (m, 4H), 3.69 (s, 3H), 3.45 (m, 2H), 3.15-3.12 (m, 2H), 3.00-2.90 (m, 2H).

Example 7

Preparation of 3-fluoro-N-(4-hydroxy-3-(1-methyl-1H-pyrazol-5-yl)phenyl)benzamide (Compound 8)

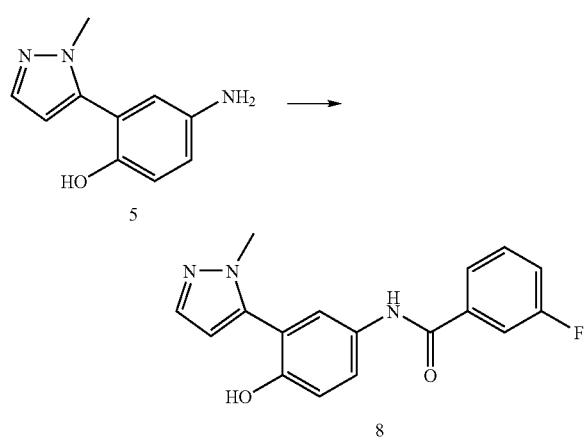

Under a nitrogen atmosphere N,N-dimethylacetamide (7.83 L) was transferred to a 30 L jacketed reaction vessel followed by 4-amino-2-(1-methyl-1H-pyrazol-5-yl)phenol (1.57 kg, 8.28 mol). The reaction was cooled to 8° C. and pyridine (0.65 kg, 8.28 mol) was added. The reaction mixture was further cooled to −6° C. and 3-fluorobenzoyl chloride (1.312 kg, 8.27 mol) was added slowly while maintaining the reaction temperature below 3° C. After completion of addition of the 3-fluorobenzoyl chloride, the mixture was stirred at 0-5° C. for 15 min and then at 20° C. for 75 min. LCMS analysis of a reaction sample indicated complete conversion to the product. Water (19.58 L) was added slowly while maintaining the reaction temperature at 535° C. The product precipitated out and the slurry was stirred at 28° C. for 15 min and then filtered. The solid cake was washed with water (20 L) followed by heptane (2×4 L) and dried in at 60° C. under house vacuum to obtain compound (8) (2.766 kg containing 5.5% water, 101%). $^1$H NMR (DMSO-d$_6$) δ 10.2 (s, 1H), 9.86 (s, 1H), 7.83 (d, J=4 Hz, 1H), 7.79 (d, J=8 Hz, 1H), 7.70 (d, J=8 Hz, 1H), 7.62 (m, 2H), 7.47 (m, 2H), 7.01 (d, J=8 Hz, 1H), 3.72 (s, 3H).

Example 8

Preparation of 4-acetyl-1-(2-(4-(3-fluorobenzamido)-2-(1-methyl-1H-pyrazol-5-yl)phenoxy)ethyl)piperazin-1-ium carboxyformate (Compound 9)

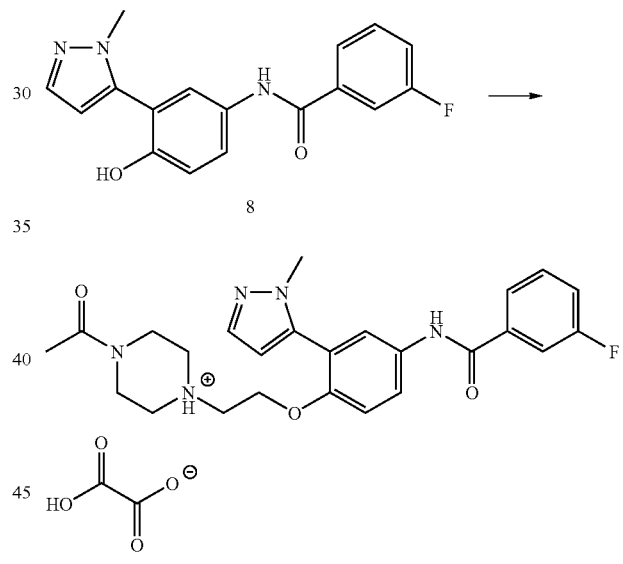

Under a nitrogen atmosphere, THF (18 L) was transferred to a 30 L jacketed reaction vessel. 3-Fluoro-N-(4-hydroxy-3-(1-methyl-1H-pyrazol-5-yl)phenyl)benzamide (1.82 kg, 5.84 mol), triphenylphosphine (2.30 kg, 8.77 mol) and 1-(4-(2-hydroxyethyl)piperazin-1-yl)ethanone (1.550 kg of 76.2% purity, 6.85 mol) were added. The reaction was cooled to 15° C. and diisopropyl azodicarboxylate (1.77 kg, 8.77 mol) was added slowly maintaining the internal temperature below 30° C. The reaction was cooled to 20° C. and stirred for 2 hours. Additional amounts of triphenylphosphine (0.77 kg, 2.92 mol), 1-(4-(2-hydroxyethyl)piperazin-1-yl)ethanone (0.503 kg of 76.2% purity, 2.23 mol) and diisopropyl azodicarboxylate (0.59 kg, 2.92 mol) were added and the reaction was stirred for an additional 30 minutes. Triphenylphosphine (1.53 kg, 5.84 mol) and diisopropyl azodicarboxylate (1.18 kg, 5.85 mol) were added and the reaction was stirred for a further 35 minutes. Additional amounts of triphenylphosphine (0.77 kg, 2.92 mol) and diisopropyl azodicarboxylate (0.59 kg, 2.92 mol) were added and the reaction was stirred for a further 10 minutes. LCMS analysis of a reaction sample indicated conversion to the product and the starting material was not detected. The reaction was stirred overnight at room temperature. THF (approximately 14.4 L) was distilled under reduced pressure and ethanol (8 L) was added. The residual THF was removed by distillation (solvent swap method). An additional amount of ethanol (9 L) was transferred into the reactor followed by a solution of oxalic acid (0.74 kg, 8.18 mol) in ethanol (3 L) and then by water (4 L). The oxalate salt of 3-fluoro-N-[3-(2-methyl-2H-pyrazol-3-yl)-4-(2-N-acetyl-piperazinyl-4-yl-ethoxy)-phenyl]-benzamide crystallized out after stirring the mixture at 20° C. for 2.5 hours. The crystallized product was filtered, washed with ethanol (2×2.5 L) and dried at 60° C. under house vacuum to afford compound (9) (1.70 kg, 52%). $^1$H NMR (DMSO-d$_6$) δ 10.32 (s, 1H), 7.82 (m, 3H), 7.70 (d, J=4 Hz, 1H), 7.60 (m, 2H), 7.46 (m, 2H), 7.20 (d, J=4 Hz, 1H), 4.17 (t, J=8 Hz, 2H) 3.70 (s, 3H), 3.40 (m, 4H), 2.82 (t, J=4 Hz, 2H), 2.49 (m, 2H), 2.43 (t, J=4 Hz, 2H), 1.98 (s, 3H).

Example 9

Preparation of N-(3-(3-(dimethylamino)acryloyl)-4-hydroxyphenyl)acetamide (Compound 11)

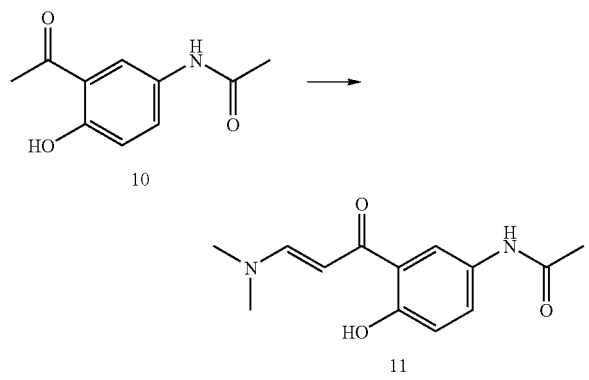

A stirred mixture of N-(3-acetyl-4-hydroxyphenyl)acetamide (148.8 g, 0.770 mol), dimethylformamide dimethylacetal (206.2 mL, 185.0 g, 1.552 mol), and 2-propanol (1500 mL) was heated to 45° C. under nitrogen. After the mixture had been stirred at 45° C. for about 18 hours, conversion of N-(3-acetyl-4-hydroxyphenyl)acetamide to N-(3-(3-(dimethylamino)acryloyl)-4-hydroxyphenyl)acetamide was >98% by HPLC peak area. Water (1500 mL) was added, and 1500 mL of solvent was then removed by distillation under reduced pressure at 55° C. The reactor contents were cooled to 15° C. and then filtered. The filter cake was dried under reduced pressure at 65° C. to provide compound (11) (167.0 g, 87%), (>98% purity by HPLC peak area purity). $^1$H NMR. (DMSO-d$_6$): δ 14.07 (s, 1H), 9.80 (s, 1H), 8.00 (d, J=2.5 Hz, 1H), 7.95 (d, J=12.0 Hz, 1H), 7.56 (dd, J$_1$=8.8, J$_2$=2.5 Hz, 1H), 6.79 (d, J=8.8 Hz, 1H), 5.75 (d, J=12.0 Hz, 1H), 3.25 (s, 3H), 3.00 (s, 3H), 2.03 (s, 3H).

Example 10

Preparation of 5-(2'-hydroxy-5'-acetamidophenyl)-1-methyl-1H-pyrazole (Compound 4)

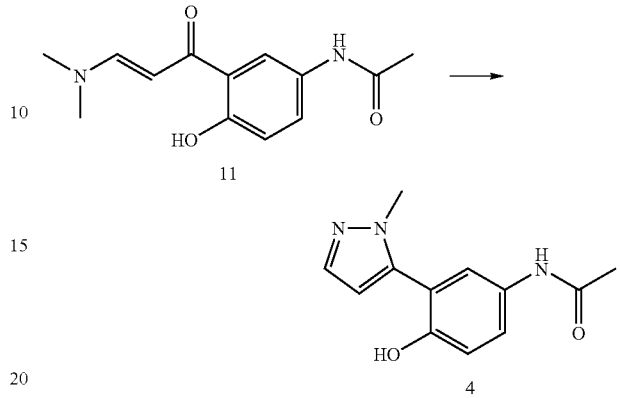

N-(3-(3-(dimethylamino)acryloyl)-4-hydroxyphenyl)acetamide (51.6 g, 208 mmol) and then boron trifluoride diethyletherate (5.22 mL, 5.85 g, 41.2 mmol) were added to a flask containing methanol (502 mL) stirred at ambient temperature under nitrogen. While the resulting mixture was stirred at 2-4° C. under nitrogen, methylhydrazine (15.32 mL 13.27 g) was added. After the reactor contents had been stirred overnight at 5° C., conversion of N-(3-(3-(dimethylamino)acryloyl)-4-hydroxyphenyl)acetamide to an 87.9:12.1 mixture of compound (4) and its regioisomer 3-(2'-hydroxy-5'-acetamidophenyl)-1-methyl-1H-pyrazole was >99.5% by HPLC peak area. Most of the methanol was then removed by distillation under reduced pressure with a 30° C. jacket temperature. Heptane (250 mL) was added to the oily residue, and distillation of solvent under reduced pressure was continued until solids began to precipitate. A mixture of heptane (126 mL) and ethyl acetate (377 mL) was added, and the resulting suspension was stirred at ambient temperature for two hours. The solid product was filtered and resuspended in water (377 mL) premixed with 37 wt. % aqueous hydrochloric acid (1.57 mL, 1.89 g, 19.1 mmol). The resulting suspension was stirred for two hours at ambient temperature and then filtered. The filtered solid was dried under reduced pressure at 65° C. to provide compound (4) (39.4 g, 82%), (>99% HPLC peak area purity). $^1$H NMR (DMSO-d$_6$): δ 9.80 (s, 1H), 9.69 (s, 1H), 7.43 (dd, J$_1$=8.8, J$_2$=2.6 Hz, 1H), 7.42 (d, J=0.7 Hz, 2H), 6.89 (dd, J$_1$=8.0, J$_2$=1.0 Hz, 1H), 6.20 (d, J=1.81 Hz, 1H), 3.66 (s, 3H), 1.99 (s, 3H).

Example 11

Preparation of 4-amino-2-(1-methyl-1H-pyrazol-5-yl)phenol (Compound 5)

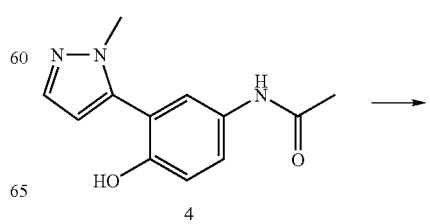

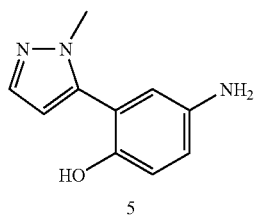

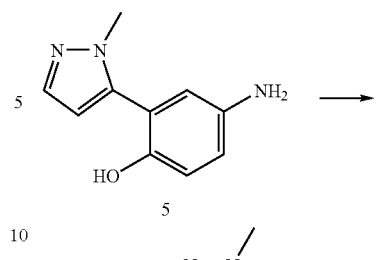

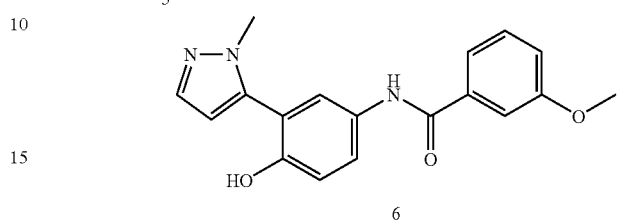

To a flask containing a mixture of N-(4-hydroxy-3-(1-methyl-1H-pyrazol-5-yl)phenyl)acetamide (4, 39.1 g, 169 mmol) and methanol (170 mL) stirred under nitrogen was added concentrated sulfuric acid (23 mL, 42.3 g, 431 mmol) slowly. When the addition was complete, the reaction mixture was a clear solution at 55° C. After the stirred reaction mixture had been refluxed under nitrogen for seven hours, most of the methanol was then distilled off at reduced pressure with a 70° C. bath. After water (80 mL) had been added to the distillation residue, most of the water was then distilled off the product mixture at reduced pressure with a 70° C. bath. The methanol content of the distillation residue was determined by $^1$H-NMR integration to be about 7.7 wt. % of the compound 5 content. After more water (80 mL) had been added to the distillation residue, most of the water was then again distilled off the product mixture at reduced pressure with a 70° C. bath. The methanol content of the distillation residue was determined by $^1$H-NMR integration to be about 2.2 wt. % of the compound 5 content. The distillation residue was diluted with additional water (80 mL), and aqueous sodium hydroxide (50 wt. %, 41 mL, 62.5 g, 782 mmol) was added while the stirred product mixture was maintained at 30-35° C. with a cooling bath. During the addition, the product began to precipitate, and the pH of the product mixture rose to 5.8-6.1. Saturated aqueous sodium bicarbonate (50 ml-53.2 g, 55.7 mmol) was then added while the stirred product mixture was maintained at about 25° C. with a cooling bath. The pH of the product mixture increased to 7 as a result. After the product mixture had been stirred at about 23° C. for two hours, its pH dropped to 6.2. After an additional hour of stirring at about 23° C., more saturated aqueous sodium bicarbonate (25 mL, 26.6 g, 27.9 mmol) was added, and the pH of the product mixture increased to 7 as a result. After an additional half hour of stirring at 23° C., the product mixture was filtered. The solid filter cake was washed with water (3×80 mL) and vacuum dried at 60° C. to constant weight to provide compound 5 (29.7 g, 93% yield, 99.40% pure by HPLC area).

Example 12

Preparation of 4-(2-(4-(3-Methoxybenzamido)-2-(1-methyl-1H-pyrazol-5-yl)phenoxy)ethyl)morpholin-4-ium chloride (Compound 7)

Step A: Preparation of N-(4-hydroxy-3-(1-methyl-1H-pyrazol-5-yl)phenyl)-3-methoxybenzamide (Compound 6)

To a mixture of 4-amino-2-(1-methyl-1H-pyrazol-5-yl)phenol (5, 50.0 g, 264.3 mmol, 1.00 eq.), sodium bicarbonate (28.9 g, 344 mmol, 1.30 eq.), and 2-propanol (200 mL) stirred under nitrogen was added 3-methoxybenzoyl chloride (49.6 g, 290.8 mmol, 1.10 eq.) sufficiently slowly to maintain the reaction mixture at 0-5° C. with reactor jacket cooling. After the resulting brown solution had been stirred at 5° C. for one hour and at 10-15° C. for an additional hour, water (300 mL) was added sufficiently slowly to maintain the stirred reaction mixture at 20-25° C. with reactor jacket cooling. The reaction mixture was stirred at about 23° C. for two more hours and then filtered. The solid filter cake was washed with water (3×150 mL) and vacuum dried at 65° C. for about 16 hours and then at 75-80° C. to constant weight to provide compound 6 (80 g, 247 mmol, 93.6% yield, 99.24% pure by HPLC area). Water content of 6 prepared by this procedure is typically about 0.1 wt %.

Step B: Preparation of 4-(2-(4-(3-Methoxybenzamido)-2-(1-methyl-1H-pyrazol-5-yl)phenoxy)ethyl)morpholin-4-ium chloride (Compound 7)

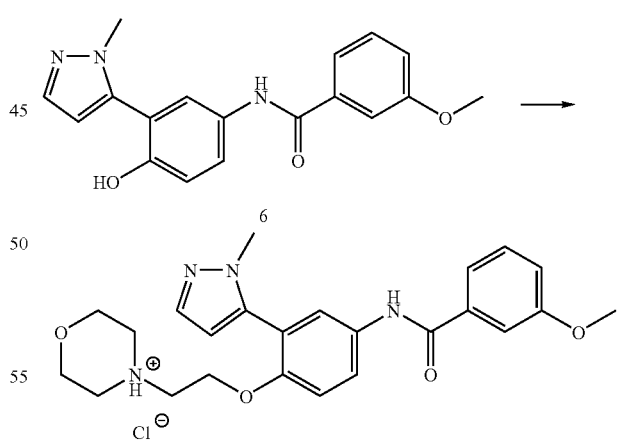

A mixture of N-(4-hydroxy-3-(1-methyl-1H-pyrazol-5-yl)phenyl-3-methoxybenzamide prepared by the method of Example 12, Step A (6, 50.0 g, 154.6 mmol, 1.00 eq.) and tetrahydrofuran (THF, 500 mL) was stirred and heated to achieve dissolution of 6. The resulting solution was cooled to about 25° C., and triphenylphosphine (52.7 g, 200.9 mmol, 1.30 eq.) was added. After the resulting solution had been cooled to −5° C. to 0° C., diisopropyl azodicarboxylate (40.6 g, 200.8 mmol, 1.30 eq.) was added sufficiently slowly to maintain the stirred reaction mixture at −5° C. to 0° C. with external reactor cooling. The resulting mixture was stirred at about 23° C. for four hours and then cooled to 15° C. 2-Morpholinoethanol (28.4 g, 216.5 mmol, 1.40 eq.) was then added, causing the stirred reaction mixture to warm to about 23° C., at which temperature stirring was continued for two hours. Most of the THF was distilled off the reaction mixture at reduced pressure and at ≦60° C. 2-Propanol (600 mL) was added, and then most of the 2-propanol was distilled off the product mixture at reduced pressure and at ≦60° C. Additional 2-propanol (600 mL) was added, and the resulting mixture was heated to 60° C. Concentrated aqueous hydrochloric acid (25.8 g, 21.46 mL, 261 mmol, 1.69 eq.) was added to the stirred 60° C. solution to achieve a pH of 2.0. The product mixture was then cooled to about 23° C. and stirred at that temperature for three hours. The slurry of precipitated product was filtered, and the filtered solid was washed with 2-propanol (3×150 mL) and then vacuum dried at 65° C. to constant weight to provide 7 (66.18 g, 139.9 mmol, 90.5% yield, 99.24% pure by HPLC area).

Example 13

Purification of 4-acetyl-1-(2-(4-(3-fluorobenzamido)-2-(1-methyl-1H-pyrazol-5-yl)phenoxy)ethyl)piperazin-1-ium carboxyformate (Compound 9)

9

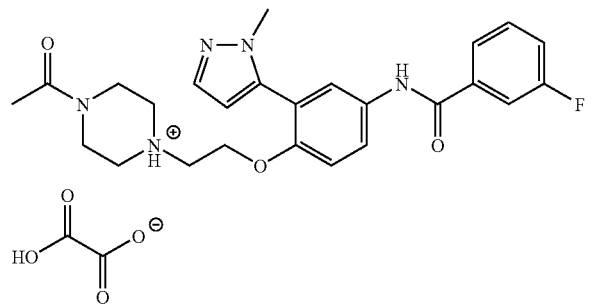

A mixture of 1.70 kg of 9 (1.70 kg, prepared according to Example 8) and an additional portion of 9 (800g, similarly prepared but not dried under reduced pressure) was purified as follows. A mixture of both portions of 9, purified water (11.1 kg), and ethanol (7.10 kg) was stirred and heated to reflux (84.3° C.) to achieve partial dissolution. About 4 L of solvent was then distilled off, and the stirred mixture was cooled to 20-22° C. The solid product was recovered by suction filtration, washed with ethanol (0.710 kg), and dried under reduced pressure at 60° C. to constant weight to provide the title compound (2.13 kg, 49% yield from 8, 99.1% purity by HPLC peak area).

Those skilled in the art will recognize that various modifications, additions, substitutions, and variations to the illustrative examples set forth herein can be made without departing from the spirit of the invention and are, therefore, considered within the scope of the invention. All documents referenced above, including, but not limited to, printed publications, and provisional and regular patent applications, are incorporated herein by reference in their entirety.

What is claimed is:
1. A process for preparing a compound of Formula (I):

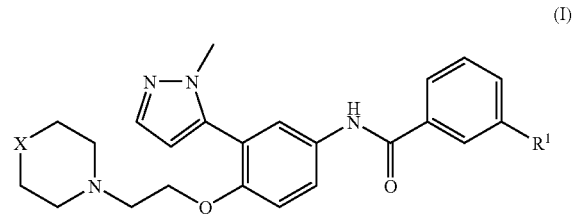

(I)

or a salt form thereof,
wherein:
$R^1$ is $C_1$-$C_8$ alkyl, halo, $C_1$-$C_8$ haloalkyl or $C_1$-$C_8$ alkoxy;
X is O, S, $NR^2$ or $CHR^2$; and
$R^2$ is H, $C_1$-$C_8$ alkyl, $C_1$-$C_8$ acyl, $C_1$-$C_8$ alkenyl, $C_1$-$C_8$ alkynyl, $C_3$-$C_7$ cycloalkyl, $C_1$-$C_8$ haloalkyl, arylalkyl, aryl, heteroaryl or heteroarylalkyl each optionally substituted with $C_1$-$C_8$ alkyl, halo, $C_1$-$C_8$ haloalkyl or $C_1$-$C_8$ alkoxy;
comprising reacting a compound of Formula (II):

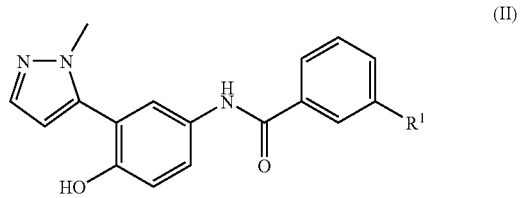

(II)

with a compound of Formula (III):

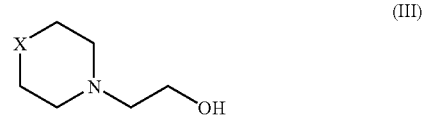

(III)

in the presence of a trisubstituted phosphine and a compound having the Formula (A):

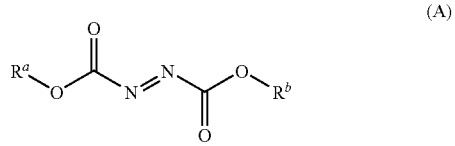

(A)

wherein:
$R^a$ and $R^b$ are each, independently, $C_1$-$C_{10}$ alkyl or $C_1$-$C_7$ cycloalkyl;
to form said compound of Formula (I).
2. The process of claim 1, wherein $R^1$ is methoxy and X is O.
3. The process according to claim 1, wherein said trisubstituted phosphine is triphenylphosphine.
4. The process according to claim 1, wherein $R^a$ and $R^b$ are each, independently, $C_1$-$C_4$ alkyl.
5. The process according to claim 4, wherein $R^a$ and $R^b$ are both prop-2-yl.

6. The process according to claim 1, wherein said reacting is carried out at a temperature of about −50° C. to about 75° C.

7. The process according to claim 6, wherein said reacting is carried out at a temperature of about 0° C. to about 25° C.

8. The process according to claim 1, wherein said reacting is carried out in an ether-forming solvent.

9. The process according claim 8, wherein said ether-forming solvent comprises tetrahydrofuran.

10. The process according to claim 1, wherein the molar ratio of said compound of Formula (A) to said compound of Formula (II) is about 4:1 to about 1:1.

11. The process according to claim 10, wherein the molar ratio of said compound of Formula (A) to said compound of Formula (II) is about 1.6:1 to about 1.4:1.

12. The process according to claim 1, wherein the molar ratio of said trisubstituted phosphine to said compound of Formula (II) is about 4:1 to about 1:1.

13. The process according to claim 12, wherein the molar ratio of said trisubstituted phosphine to said compound of Formula (II) is about 1.6:1 to about 1.4:1.

14. The process according to claim 1, wherein the molar ratio of said compound of Formula (A) to said trisubstituted phosphine is about 1:1.

15. The process according to claim 1, wherein the molar ratio of said compound of Formula (III) to said compound of Formula (II) is about 2.5:1 to about 0.5:1.

16. The process according to claim 15, wherein the molar ratio of said compound of Formula (III) to said compound of Formula (II) is about 2:1 to about 1:1.

17. The process according to claim 1, wherein said compound of Formula (II) is prepared by the method comprising reacting a compound of Formula (IV):

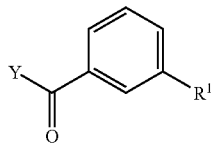

(IV)

wherein:
$R^1$ is $C_1$-$C_8$ alkyl, halo, $C_1$-$C_8$ haloalkyl or $C_1$-$C_8$ alkoxy;
Y is halo, OH or $OC(O)R^3$; and
$R^3$ is $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, arylalkyl, aryl, heteroaryl or heteroarylalkyl each optionally substituted with $C_1$-$C_8$ alkyl, halo, $C_1$-$C_8$ haloalkyl or $C_1$-$C_8$ alkoxy;

with a compound of Formula (V):

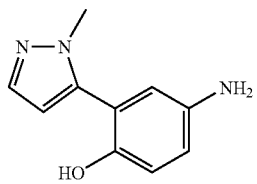

(V)

or a salt thereof to form said compound of Formula (II).

18. The process according to claim 17, wherein said compound of Formula (V) or a salt thereof is prepared by the method comprising reacting a compound of Formula (VI):

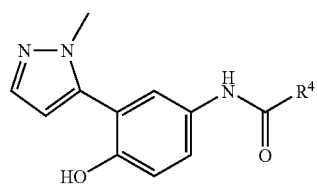

(VI)

wherein:
$R^4$ is $C_1$-$C_8$ alkyl, $C_1$-$C_8$ alkenyl, $C_1$-$C_8$ alkynyl, $C_3$-$C_7$ cycloalkyl, arylalkyl, aryl, heteroaryl or heteroarylalkyl each optionally substituted with $C_1$-$C_8$ alkyl;

with a cleaving reagent to form said compound of Formula (V) or a salt thereof.

19. The process according to claim 18, wherein said compound of Formula (VI) is prepared by the method comprising reacting a compound of Formula (VII):

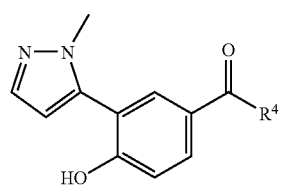

(VII)

wherein:
$R^4$ is $C_1$-$C_8$ alkyl, $C_1$-$C_8$ alkenyl, $C_1$-$C_8$ alkynyl, $C_3$-$C_7$ cycloalkyl, arylalkyl, aryl, heteroaryl or heteroarylalkyl each optionally substituted with $C_1$-$C_8$ alkyl;

with an amine in the presence of an acid to form said compound of Formula (VI).

20. The process according to claim 18, wherein said compound of Formula (VI) is prepared by the method comprising reacting a compound of Formula (VIII):

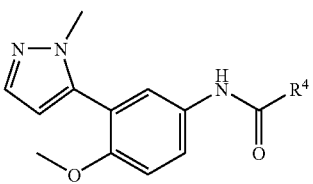

(VIII)

wherein:
$R^4$ is $C_1$-$C_8$ alkyl, $C_1$-$C_8$ alkenyl, $C_1$-$C_8$ alkynyl, $C_3$-$C_7$ cycloalkyl, arylalkyl, aryl, heteroaryl or heteroarylalkyl each optionally substituted with $C_1$-$C_8$ alkyl;

with a demethylating agent to form said compound of Formula (VI).

21. The process according to claim 18, wherein said compound of Formula (VI) is prepared by the method comprising reacting a compound of Formula (XIV):

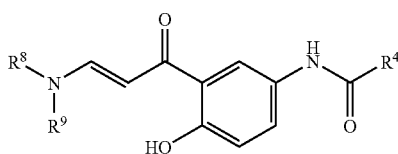

(XIV)

wherein:
$R^8$ and $R^9$ are each independently $C_1$-$C_8$ alkyl or arylalkyl; or $R^8$ and $R^9$ together with the nitrogen atom to which they are both bonded form a heterocyclyl or a heterobicyclyl group;
with methyl hydrazine in the presence of a catalyst to form said compound of Formula (VI).

22. The process according to claim 21, wherein said compound of Formula (XIV) is prepared by the method comprising reacting a compound of Formula (XV):

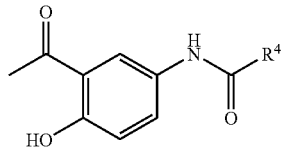

(XV)

wherein:
$R^4$ is $C_1$-$C_8$ alkyl, $C_1$-$C_8$ alkenyl, $C_1$-$C_8$ alkynyl, $C_3$-$C_7$ cycloalkyl, arylalkyl, aryl, heteroaryl or heteroarylalkyl each optionally substituted with $C_1$-$C_8$ alkyl;
with a compound of Formula (XVI):

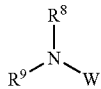

(XVI)

wherein:
$R^8$ and $R^9$ are each independently $C_1$-$C_8$ alkyl or arylalkyl; or
$R^8$ and $R^9$ together with the nitrogen atom to which they are both bonded form a heterocyclyl or a heterobicyclyl group;
W is formyl or -CH(OR$^{10}$)(OR$^{11}$);
and $R^{10}$ and $R^{11}$ are each independently $C_1$-$C_8$ alkyl;
to form said compound of Formula (XIV).

23. A process for preparing a salt of a compound of Formula (I):

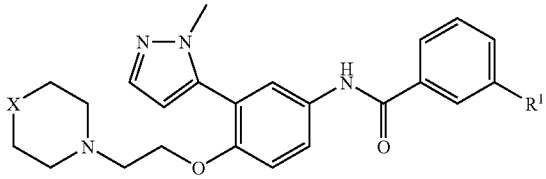

(I)

wherein:
$R^1$ is $C_1$-$C_8$ alkyl, halo, $C_1$-$C_8$ haloalkyl or $C_1$-$C_8$ alkoxy;
X is O, S, NR$^2$ or CHR$^2$; and
$R^2$ is H, $C_1$-$C_8$ alkyl, $C_1$-$C_8$ acyl, $C_1$-$C_8$ alkenyl, $C_1$-$C_8$ alkynyl, $C_3$-$C_7$ cycloalkyl, $C_1$-$C_8$ haloalkyl, arylalkyl, aryl, heteroaryl or heteroarylalkyl each optionally substituted with $C_1$-$C_8$ alkyl, halo, $C_1$-$C_8$ haloalkyl or $C_1$-$C_8$ alkoxy;
comprising reacting said compound of Formula (I) with a salt-forming acid to form said salt of a compound of Formula (I).

24. The process of claim 23, wherein $R^1$ is methoxy and X is O.

25. The process according to claim 24, wherein said reacting is carried out in a salt-forming solvent.

26. The process according to claim 25, wherein said salt-forming solvent comprises isopropanol.

27. The process according to claim 25, wherein said salt-forming solvent comprises ethanol.

28. The process according to claim 23, wherein said reacting is carried out at a temperature of about −10° C. to about reflux temperature.

29. The process according to claim 28, wherein said reacting is carried out at a temperature of about 20° C. to about 80° C.

30. The process according to claim 23, wherein said salt-forming acid is hydrochloric acid.

31. The process according to claim 23, wherein said salt is a hydrochloride salt.

32. The process according to claim 23, wherein said salt-forming acid is oxalic acid.

* * * * *